United States Patent [19]

Nakatsukasa

[11] Patent Number: 4,695,545
[45] Date of Patent: * Sep. 22, 1987

[54] CULTURE AND PROCESS FOR PRODUCING A41030 ANTIBIOTICS

[75] Inventor: Walter M. Nakatsukasa, Indianapolis, Ind.

[73] Assignee: Eli Lilly and Company, Indianapolis, Ind.

[*] Notice: The portion of the term of this patent subsequent to Aug. 5, 2003 has been disclaimed.

[21] Appl. No.: 607,907

[22] Filed: May 7, 1984

Related U.S. Application Data

[63] Continuation of Ser. No. 361,302, Mar. 24, 1982, abandoned.

[51] Int. Cl.$^4$ .................. C12P 17/18; C12P 21/04; C12P 17/00; C12P 17/16; C12N 1/20; C12R 1/465; A61K 35/00; C07K 15/00
[52] U.S. Cl. ..................... 435/119; 435/71; 435/117; 435/118; 435/253; 435/886; 530/317; 530/329; 424/118; 424/119; 424/120
[58] Field of Search .............. 424/118, 119, 120; 435/119, 41, 117, 118, 253, 886, 71; 530/317, 329

[56] References Cited

U.S. PATENT DOCUMENTS

| 3,017,272 | 1/1962 | Van Dijck et al. | 99/2 |
| 3,067,099 | 12/1962 | McCormick | 167/65 |
| 3,338,786 | 8/1967 | Kunstmann et al. | 167/65 |
| 3,700,768 | 10/1972 | Kunstmann et al. | 424/118 |
| 3,952,095 | 4/1976 | Hamill et al. | 424/118 |
| 4,322,343 | 3/1982 | Debono | 260/112.5 R |
| 4,537,770 | 8/1985 | Michel et al. | 424/118 |
| 4,604,239 | 8/1986 | Michel et al. | 530/317 |

FOREIGN PATENT DOCUMENTS 0765886 6/1957 United Kingdom .

OTHER PUBLICATIONS

Williamson et al., "Structure Revision of the Antibiotic Vancomycin, The Use of Nuclear Overhauser Effect Difference Spectroscopy", J. Am. Chem. Soc. 103, 6580–6585 (1981).
Kalman et al., "An NMR Study of the Antibiotic Ristocetin A., The Negative Nuclear Overhauser Effect in Structure Elucidation", J. Am. Chem Soc. 102, 897–905 (1980).
Ellestad et al., "Avoparcin and Epiavoparcin", J. Am. Chem. Soc. 103, 6522–6524 (1981).
The American Type Culture Collection Catalog (1978) pp. 174–175.
CRC Handbook of Microbiology, vol. 3: Microbial Products, A. I. Laskin and H. A. Lechevalier, Eds., CRC Press, Cleveland, OH, 1973, pp. 724, 755, 816, 888 and 947

Primary Examiner—James Martinell
Attorney, Agent, or Firm—Nancy J. Harrison; Leroy Whitaker

[57] ABSTRACT

A hitherto undescribed microorganism, Streptomyces virginiae NRRL 12525, which upon culturing produces the A41030 antibiotic complex comprising several factors. The A41030 antibiotics produced show antibacterial activity against the gram-positive genera Staphylococcus and Streptococcus which are resistant to penicillin. In addition, these antibiotic act to promote growth and improve feed efficiency in ruminant animals, poultry and swine, and other livestock, and to improve milk production in ruminant animals.

4 Claims, 7 Drawing Figures

CULTURE AND PROCESS FOR PRODUCING A41030 ANTIBIOTICS

This application is a continuation of application Ser. No. 361,302 filed Mar. 24, 1982, now abandoned.

SUMMARY OF THE INVENTION

This invention relates to an axenic culture of the microorganism *Streptomyces virginiae* NRRL 12525, and to the use of NRRL 12525 for the production of the antibiotic A41030 complex, which is comprised of individual factors A, B, C, D, E, F, and G. This complex is produced by culturing the hitherto undescribed microorganism, *Streptomyces virginiae* NRRL 12525, or an A41030-producing mutant or variant thereof, under submerged aerobic fermentation conditions.

These A41030 antibiotics inhibit the growth of certain pathogenic microorganisms, in particular, those within the gram-positive genera *Staphylococcus* and *Streptococcus* which are resistant to penicillin. The antibiotics of this invention act to promote growth and improve feed efficiency in ruminant animals, poultry and swine, and other livestock, and to improve milk production in ruminant animals.

DESCRIPTION OF THE DRAWINGS

Infrared absorption spectra of A41030 factors A, B, C, D, E, F, and G are presented in the drawings as follows.

DETAILED DESCRIPTION OF THE INVENTION

Figure 1:
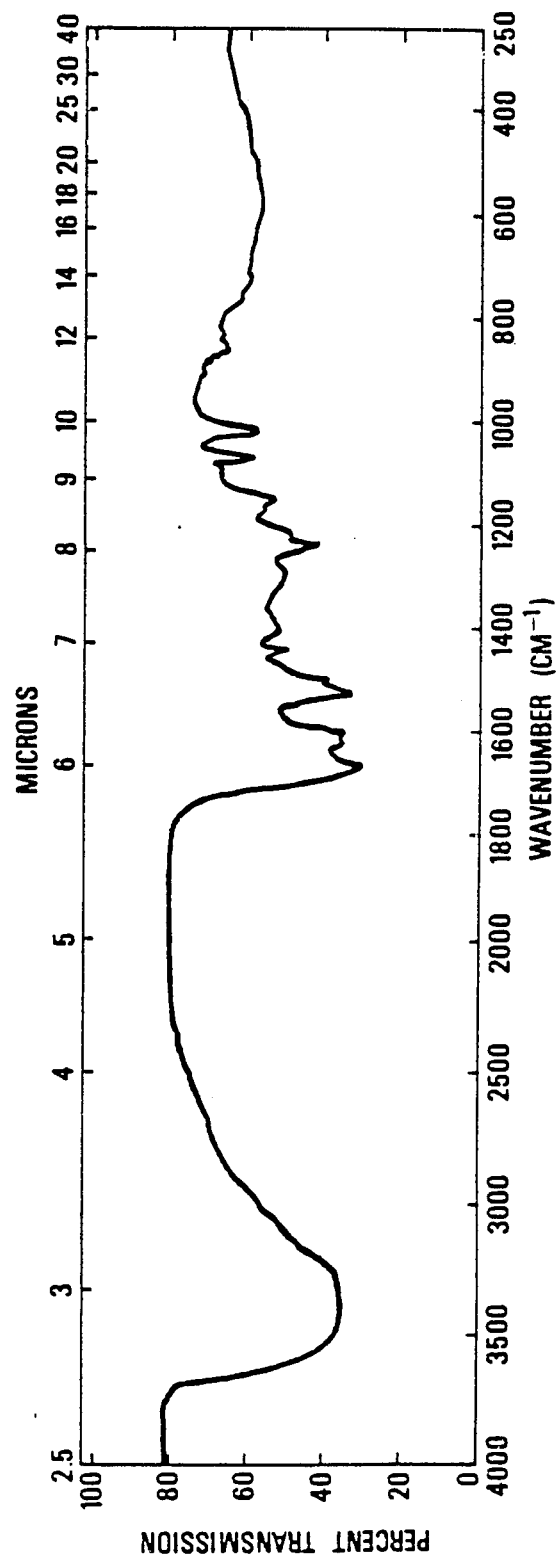
FIG. 1—A41030 factor A (in KBr pellet)
FIG. 2—A41030 factor B (in KBr pellet)
FIG. 3—A41030 factor C (in KBr pellet)
FIG. 4—A41030 factor D (in KBr pellet)
FIG. 5—A41030 factor E (in KBr pellet)
FIG. 6—A41030 factor F (in KBr pellet)
FIG. 7—A41030 factor G (in KBR pellet)

This invention relates to an axenic culture of the hitherto undescribed microorganism, *Streptomyces virginiae* NRRL 12525, which produces an antibiotic complex comprising several factors, including individual factors A, B, C, D, E, F, and G. The A41030 antibiotic complex and the individual factors A, B, C, D, E, F, and G are claimed in U.S. Pat. No. 4,537,770, issued Aug. 27, 1985. For convenience, this culture has been designated in our laboratory as culture A41030.4.

The term "complex", as used in the fermentation art, and in this specification, refers to a mixture of coproduced individual antibiotic factors. As will be recognized by those familiar with antibiotic production by fermentation, the number and ratio of the individual factors produced in an antibiotic complex will vary, depending upon the fermentation conditions and the strain used.

Culture A41030.4, which is a chemicallyinduced mutant of a strain of the *Streptomyces virginiae* culture which was initially isolated from a soil sample collected in Indianapolis, Indiana, has been deposited and made a part of the stock culture collection of the Northern Regional Research Center, U.S. Department of Agriculture, Agricultural Research Service, Peoria, Ill. 61604, from which it is available to the public under the number NRRL 12525.

Culture A41030.4 was obtained by treatment of culture A41030 with mitomycin C and N-methyl-N'-nitro-N-nitrosoguanidine.

It will be recognized by those skilled in the art that it would be possible to generate additional strains which have essentially the same biosynthetic capabilities as *Streptomyces virginiae* NRRL 12525, by subjecting culture A41030 to other mutagenic treatments. In addition to mitomycin C, other suitable agents include acriflavines, acridine orange, ethidium bromide, and similar chemical agents. Although N-methyl-N'-nitro-N-nitrosoguanidine was used, along with mitomycin C, to obtain NRRL 12525, other known mutagens such as ultraviolet rays, X-rays, high-frequency rays, radioactive rays and other chemical agents could be used to induce a similar mutagenesis.

The classification of Culture A41030.4 as a chemically-induced mutant of a strain of *Streptomyces virginiae*, is based upon a simultaneous culturing of *Streptomyces avidinii* ATCC 27419; *Streptomyces columbiensis* ATCC 27425; *Streptomyces goshikiensis* ATCC 23914; *Streptomyces griseolavendus* ATCC 25457; *Streptomyces lavendulae* ATCC 8664; *Streptomyces toxytricini* ATCC 19813; and *Streptomyces virginiae*, Grundy, Whitman, Rdzok, Hanes and Sylvester 1952, ATCC 19817. The methods and media recommended by Shirling and Gottlieb ["Methods of Characterization of *Streptomyces* species," *Int. J. Syst. Bacteriol.* 16(3), 313-340 (1966)], along with certain supplementary tests were used. Culture A41030.4 was also compared with published descriptions of the above-named strains appearing in "Bergey's Manual of Determinative Bacteriology" (8th Edition, edited by R. E. Buchanan and N. E. Gibbons, The Williams and Wilkins Co., Baltimore, Maryland); and by Shirling and Gottlieb, "Cooperative Description of Type Strains of *Streptomyces*", *Int. J. Syst. Bacteriol.* 18(2), 178 (1968).

Since Culture A41030.4 produces no aerial mycelia and no spores on any medium, it differs from all the above-named species.

CHARACTERIZATION OF A41030.4 CULTURE

Morphology

Produces no aerial mycelia and no spores.

Cultural Characteristics

The growth characteristics of culture A41030.4 on various media are presented in the following Table 1.

Color names were assigned according to the ISCC-NBS Centroid Color Charts Standard Sample No. 2106 (National Bureau of Standards, U.S. Department of Commerce, 1958), and the Color Harmony Manual, 4th Edition (Color Standards Department, Container Corporation of America, Chicago, Ill., 1958).

TABLE 1

| Medium | Cultural Characteristics on Various Media |
|---|---|
| | Characteristics |
| Yeast extract-malt extract agar (ISP medium #2) | Good growth, reverse 90. gy.Y; no aerial mycelium; no soluble pigment. |
| Oatmeal agar (ISP medium #3) | Poor growth, reverse 93. yGray; no aerial mycelium; no soluble pigment. |
| Inorganic salts-starch agar (ISP medium #4) | Poor growth, reverse 89. p. Y; no aerial mycelium; no soluble pigment. |
| Glycerol asparagine agar | Poor growth, reverse 89. |

TABLE 1-continued

Cultural Characteristics on Various Media

| Medium | Characteristics |
|---|---|
| (ISP medium #5) | p. Y; no aerial mycelium; no soluble pigment. |
| Tomato paste oatmeal agar | Good growth, reverse 54. brO; no aerial mycelium; no soluble pigment. |

The Culture A41030.4 was studied for selected physiological properties in accordance with standard procedures. The properties observed and characteristics found are recorded in Table 2, which follows:

TABLE 2

PHYSIOLOGICAL PROPERTIES OF A41030.4

Melanoid-like Pigment Production on:

| | |
|---|---|
| 1. Tryptone yeast extract broth (ISP #1) | Melanoid-like pigment |
| 2. Peptone yeast extract iron agar slants (ISP #6) | Melanoid-like pigment |
| 3. Tyrosine agar slants (ISP #7) | No melanoid-like pigment |
| Nitrate Reduction | Negative reaction |
| Gelatin Liquefaction | Negative reaction |
| NaCl Tolerance | 3% |
| Starch Hydrolysis | Negative reaction |
| Skim Milk | Partial hydrolysis |
| Temperature Requirements | 10–34° C. |

A comparison of the carbon utilization patterns of Culture A41030.4 and *Streptomyces virginiae* ATCC 19817 was conducted using ISP No. 9 basal medium to which filter-sterilized carbon sources were added to equal a final concentration of 1.0%. Plates were read after fourteen days incubation at 30° C. The results are set forth in Table 3, which follows:

TABLE 3

CARBON UTILIZATION PATTERNS OF A41030.4 AND *STREPTOMYCES VIRGINIAE* ATCC 19817

| Carbon Source | A41030.4 | ATCC 19817 |
|---|---|---|
| Acetate-Na | − | − |
| D-Arabinose | − | − |
| L-Arabinose | − | − |
| Cellobiose | + | + |
| D-Fructose | − | ± |
| D-Galactose | + | − |
| D-Glucose | + | + |
| i-Inositol | − | − |
| Lactose | − | − |
| D-Maltose | + | + |
| D-Mannitol | − | − |
| Melibiose | − | − |
| Raffinose | − | − |
| Rhamnose | − | − |
| D-Ribose | − | − |
| Salicin | ± | + |
| Succinate-Na | ± | + |
| Sucrose | − | − |
| D-Xylose | − | − |

Key:
− = no utilization
+ = utilization
± = partial utilization

Using hydrolyzed whole cells of the organism, the isomers of diaminopimelic acid were determined according to the method of Becker et al., Appl Microbiol. 11, 421-423 (1964). The results of this study are set forth below.

| Test | Result Observed |
|---|---|
| Isomers of 2,6-diaminopimelic acid | LL-isomer |

A comparision of the similarities and differences between Culture A41030.4 and *Streptomyces virginiae* ATCC 19817 is set forth in Table 4, which follows:

TABLE 4

COMPARISON OF CULTURE A41030.4 AND *S. VIRGINIAE* ATCC 19817

| Similarites | Differences |
|---|---|
| Carbon utilization pattern | Aerial spore mass |
| Melanoid pigment on ISP #6 | Fructose utilization |
| No melanoid pigment on ISP #7 | Galactose utilization |
| No soluble pigment production | Gelatin liquefaction |
| Nitrate reduction negative | Melanoid pigments in ISP #1 |
| Reverse color | Morphology |
| Skim milk reaction | NaCl tolerance |
| Starch reduction negative | Ribose utilization |
| | Temperature range |

The antibiotic substances of this invention are arbitrarily designated herein as A41030 antibiotics. The A41030 complex contains several individual factors which are designated A41030 factors A, B, C, D, E, F, and G. In discussions of utility, the term "A41030 antibiotic" will be used, for the sake of brevity, to denote a member selected from the group consisting of A41030 complex, and A41030 factors A, B, C, D, E, F, and G.

As many as seven antibiotic factors are recovered from the fermentation and are obtained as a mixture, the A41030 complex. It will be recognized that the ratio of the factors in the A41030 complex will vary, depending upon the fermentation conditions used. The individual factors A, B, C, D, E, F, and G are separated and isolated as individual compounds, as hereinafter described. The A41030 complex is soluble in water, dilute aqueous acid, dilute aqueous base, methanol-water mixtures, ethanol-water mixtures, dimethylformamide and dimethylformamide-water mixtures, dimethylsulfoxide, dimethylsulfoxide-water mixtures, acetonitrile, acetone, ethyl acetate, tetrahydrofuran, methylene chloride, and the like.

The following paragraphs describe the physical and spectral properties of the A41030 factors which have thus far been characterized.

A41030 FACTOR A

Antibiotic A41030 factor A is a white, crystalline solid. Elemental analysis of A41030 . factor A indicates that it has the following approximate percentage composition: 56.44% carbon, 3.58% hydrogen, 8.11% nitrogen, 23.20% oxygen, and 8.29% chlorine. As determined by field desorption and plasma desorption mass spectrometry, A41030 factor A has a molecular weight of 1231. Based on the elemental analysis and the molecular weight, an empirical formula of $C_{58}H_{44}Cl_3N_7O_{18}$ is assigned to factor A. Electrometric titration of factor A in 66% dimethylformamide in water indicated the presence of three titratable groups having $pK_a$ values of about 5.53, 7.60 and 10.37, with possibly additional $pK_a$'s > 10.5 (initial pH 7.83). Antibiotic A41030 factor A has the following specific rotation: $[\alpha]_D^{25}$ −19.6 (c, 9.0 in dimethylsulfoxide).

The infrared absorption spectrum of A41030 factor A in KBr pellet is shown in the accompanying drawings as FIG. 1. The following distinguishable absorption maxima are observed: 3448-3226 (strong, broad), 1653 (strong), 1610 (weak), 1587 (medium), 1515 (strong), 1488 (weak), 1429 (medium), 1227 (strong), 1139 (medium), 1064 (strong); and 1010 (strong) cm$^{-}$.

The ultraviolet absorption maxima of A41030 factor A in methanol:water (1:1) under acid, neutral, and basic conditions are recorded in Table 5.

TABLE 5

| | UV Spectrophotometry of A41030 Factors | |
|---|---|---|
| Factor | Acidic or Neutral max nm ($\epsilon$) | Basic max nm ($\epsilon$) |
| A | 278 (11,100) | 298 (17,200) |
| B | 278 (9,600) | 298 (16,800) |
| C | 278 (8,400) | 298 (14,000) |
| D | 278 (10,600) | 298 (19,900) |
| E | 278 (8,500) | 298 (15,500) |
| F | 278 (9,300) | 298 (14,500) |
| G | 278 (15,000) | 298 (18,000) |

Antibiotic A41030 factor A is soluble in alcohol-water mixtures, in dimethylsulfoxide, in dimethylformamide, in dimethylsulfoxide-water mixtures, in dimethylformamide-water mixtures, in dilute aqueous acid, and in dilute aqueous base.

On the basis of the observed physical chemical data, the following structure has been assigned to A41030 factor A.

remaining about 4 to about 6% by weight of the factors produced.

A41030 FACTOR B

Antibiotic A41030 factor B is a white solid, having an approximate elemental analysis as follows: 58.54% carbon, 4.21% hydrogen, 8.63% nitrogen, 5.96% chlorine, and by difference, 22.66% oxygen. Electrometric titration of factor B in 66% dimethylformamide in water indicated the presence of two titratable groups at p$K_a$ values of about 5.6 and 7.5, respectively, with possibly additional p$K_a$'s >10 (initial pH 6.22). An observed molecular weight of about 1197 was obtained using fast atom bombardment mass spectrometry. Based on elemental analysis and the observed molecular weight, an empirical formula of $C_{58}H_{45}Cl_2N_7O_{18}$ is assigned to factor B.

Figure 2:
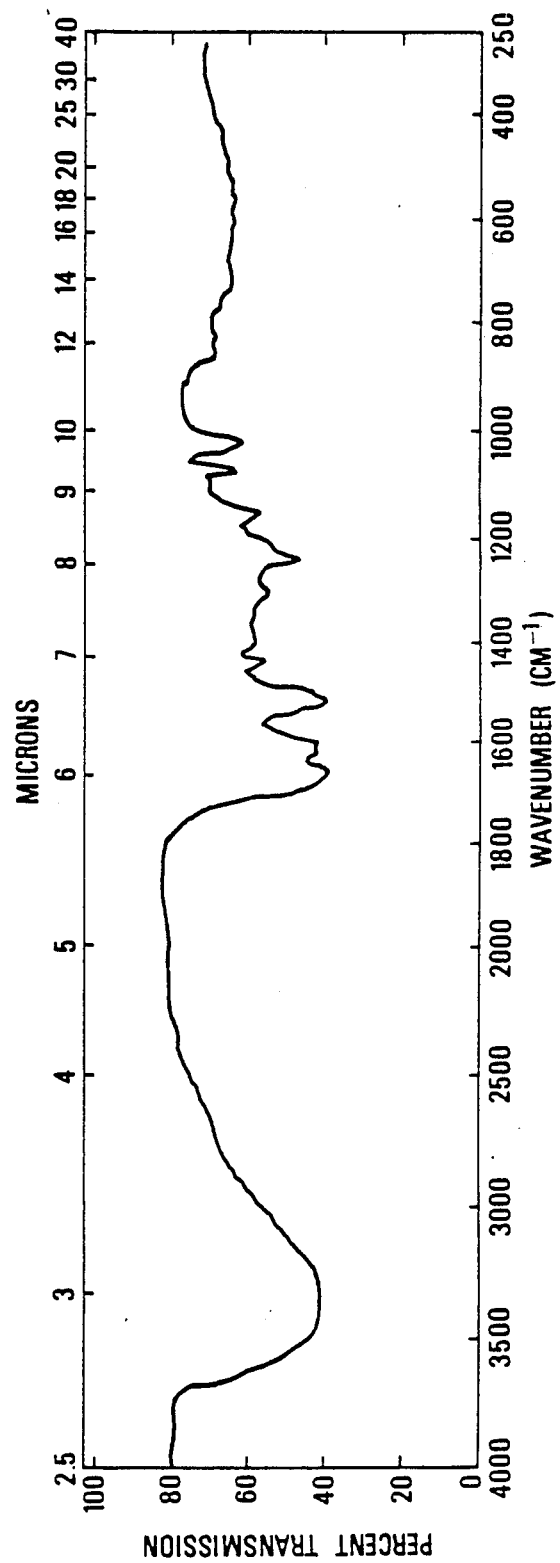

The infrared absorption spectrum of antibiotic A41030 factor B in KBr pellet is shown in the accompanying drawings as FIG. 2. The following distinguishable absorption maxima are observed: 3448-3226 (strong, broad), 1653 (strong), 1610 (medium), 1587 (weak), 1515 (strong), 1488 (weak), 1429 (medium), 1290 (weak), 1227 (strong), 1139 (medium), 1064 (strong), and 1010 (strong) cm$^{-1}$.

The ultraviolet absorption maxima of A41030 factor B in neutral, acidic, and basic methanol:water (1:1) are recorded in the foregoing Table 5.

Antibiotic A41030 factor B is soluble in the same solvents as factor A.

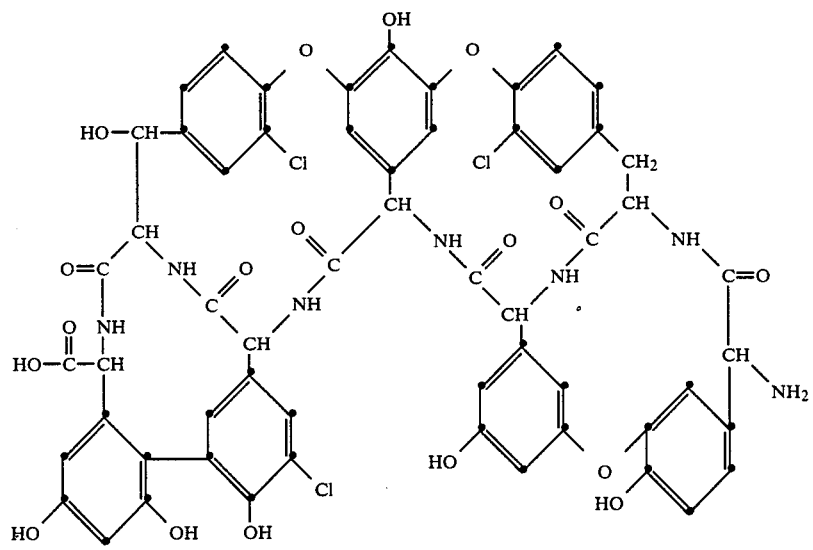

60

Using a biological assay and high performance liquid chromatography analysis, it has been found that factor A accounts for from about 94 to about 96% by weight of the antibiotic factors produced by culture A41030.4, with factors B, C, D, E, F, and G accounting for the On the basis of the observed physical chemical data, the following structure has been assigned to A41030 factor B.

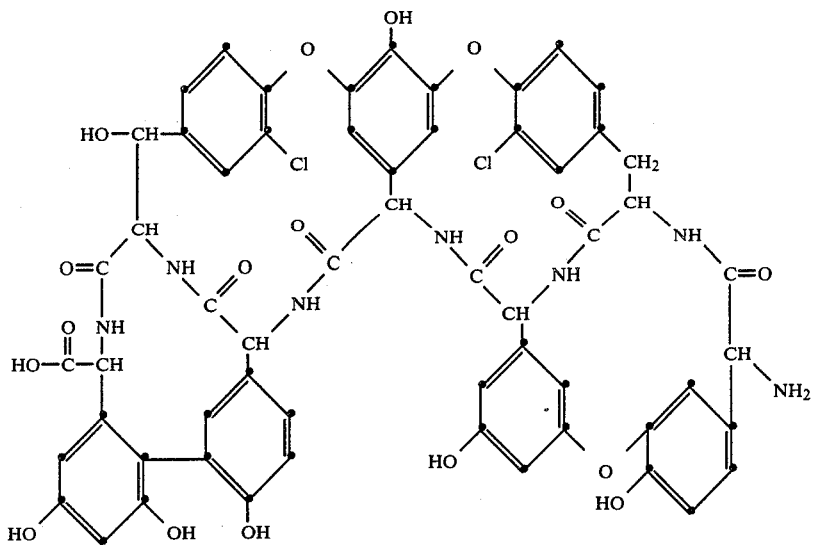

A41030 FACTOR C

Antibiotic A41030 factor C is a white solid having an approximate elemental analysis as follows: 55.08% carbon, 3.90% hydrogen, 7.03% nitrogen, 7.62% chlorine, and 26.37% oxygen. Electrometric titration of factor C in 66% dimethylformamide in water indicated the presence of two titratable groups at $pK_a$ values of about 5.5 and 7.1, respectively, with possibly additonal $PK_a$'s>10 (initial pH 6.6). An observed molecular weight of about 1393 was obtained using fast atom bombardment mass spectrometry. Based on elemental analysis and the observed molecular weight, an emprical formula of $C_{64}H_{54}Cl_3N_7O_{23}$ is assigned to factor C.

Figure 3:
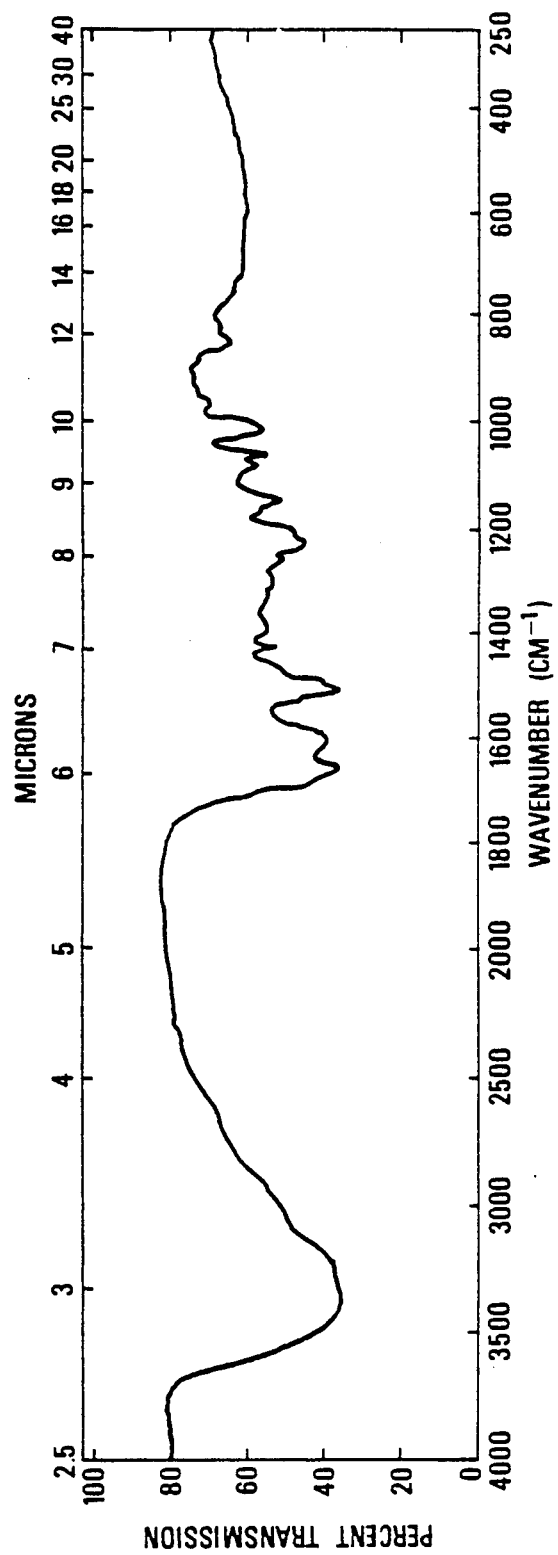

The infrared absorption spectrum of antibiotic A41030 factor C in KBr pellet is shown in the accompanying drawings as FIG. 3. The following distinguishable absorption maxima are observed: 3448-3226 (strong, broad), 1653 (strong). 1610 (medium), 1587 (weak), (strong), 1481 (weak), 1429 (medium), 1220 (strong), 1136 (strong), 1064 (weak), 1053 (medium), and 1005 (strong) $cm^{-1}$.

The ultraviolet absorption maxima of A41030 factor C in neutral, acidic, and basic methanol:water (1:1) are recorded in Table 5 above.

Antibiotic A41030 factor C is soluble in the same solvents as factor A.

On the basis of the observed physical chemical data, the structure of A41030 factor C is believed to be as follows:

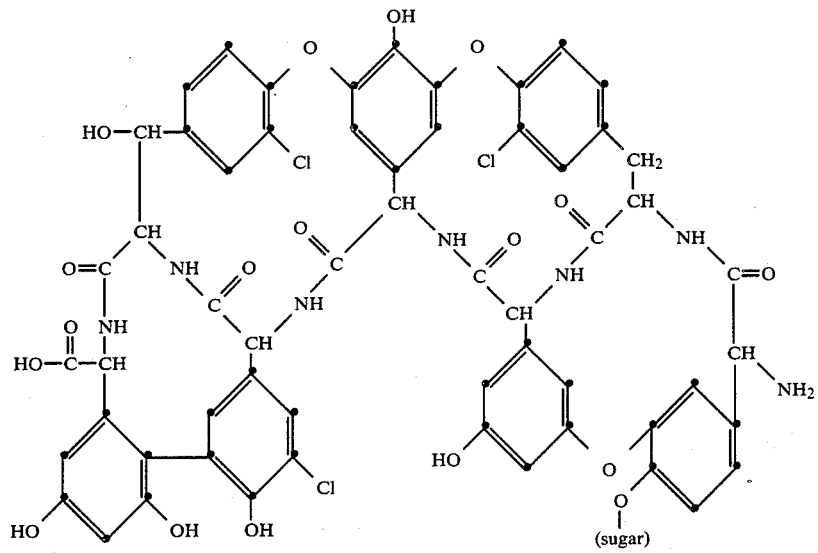

the sugar moiety being not yet identified.

A41030 FACTOR D

Antibiotic A41030 factor D is a white, amorphous solid having an approximate elemental analysis as follows: 54.46% carbon, 4.35% hydrogen, 7.58% nitrogen, 4.27% chlorine, and by difference, 29.34% oxygen. Electrometric titration of factor D in 66% dimethylformamide in water indicated the presence of two titratable groups at $pK_a$ values of about 5.5 and 7.6, respectively, with possibly additional $pK_a$'s>10 (initial pH 6.83). An observed molecular weight of about 1326 was obtained using fast atom bombardment mass spectrometry.

Figure 4:
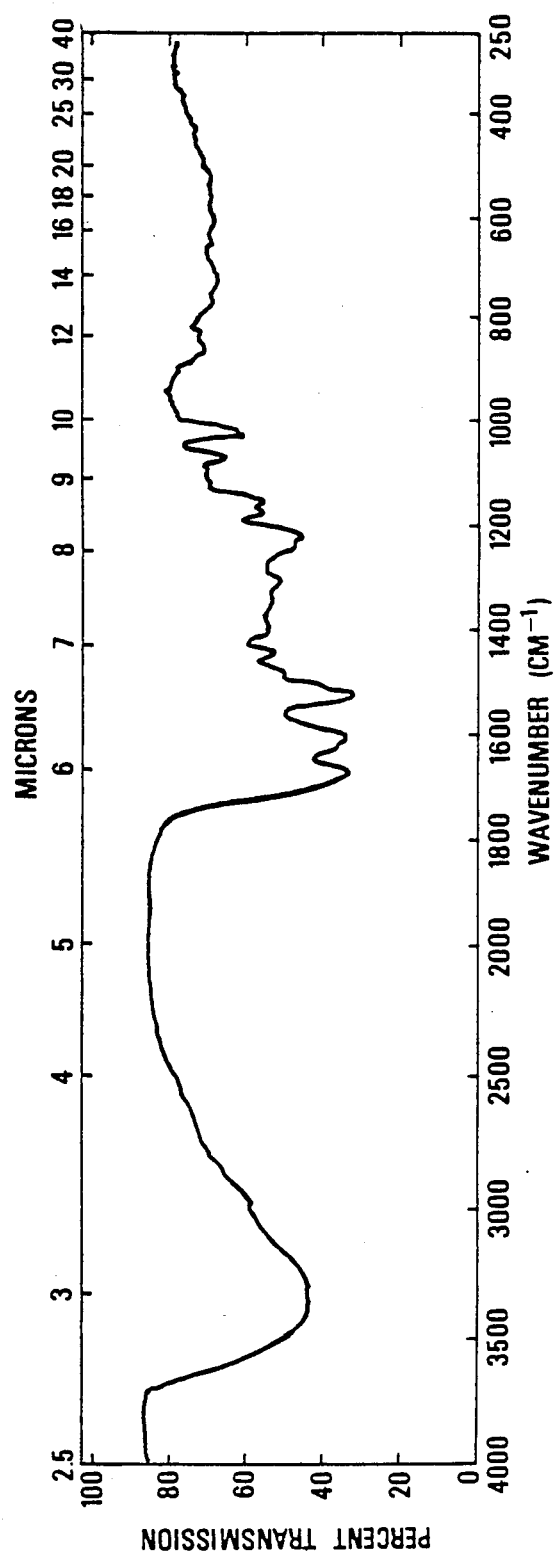

The infrared absorption spectrum of antibiotic A41030 factor D in KBr pellet is shown in the accompanying drawings as FIG. 4. The following distinguishable absorption maxima are observed: 3448–3226 (strong, broad), 2959 (weak), 1661 (strong), 1592 (strong), 1511 (strong), 1429 (weak), 1290 (weak), 1227 (weak), 1212 (medium), 1163 (weak), 1143 (weak), 1053 (medium), and 1010 (strong) cm$^{-1}$.

The ultraviolet absorption maxima of A41030 factor D in neutral, acidic, and basic methanol:water (1:1) are recorded in Table 5 above.

Antibiotic A41030 factor D is soluble in the same solvents as factor A.

On the basis of the observed physical chemical data, the structure of A41030 factor D is believed to be as follows:

and by difference, 27.85% oxygen. Electrometric titration of factor E in 66% dimethylformamide in water indicated the presence of two titratable groups at pK$_a$ values of about 5.8 and 7.7, respectively, with possibly additional pK$_a$'s>10 (initial pH 6.57). An observed molecular weight of about 1163 was obtained using fast atom bombardment mass spectrometry. A tentative empirical formula of $C_{58}H_{46}ClN_7O_{18}$ is assigned to factor E.

Figure 5:
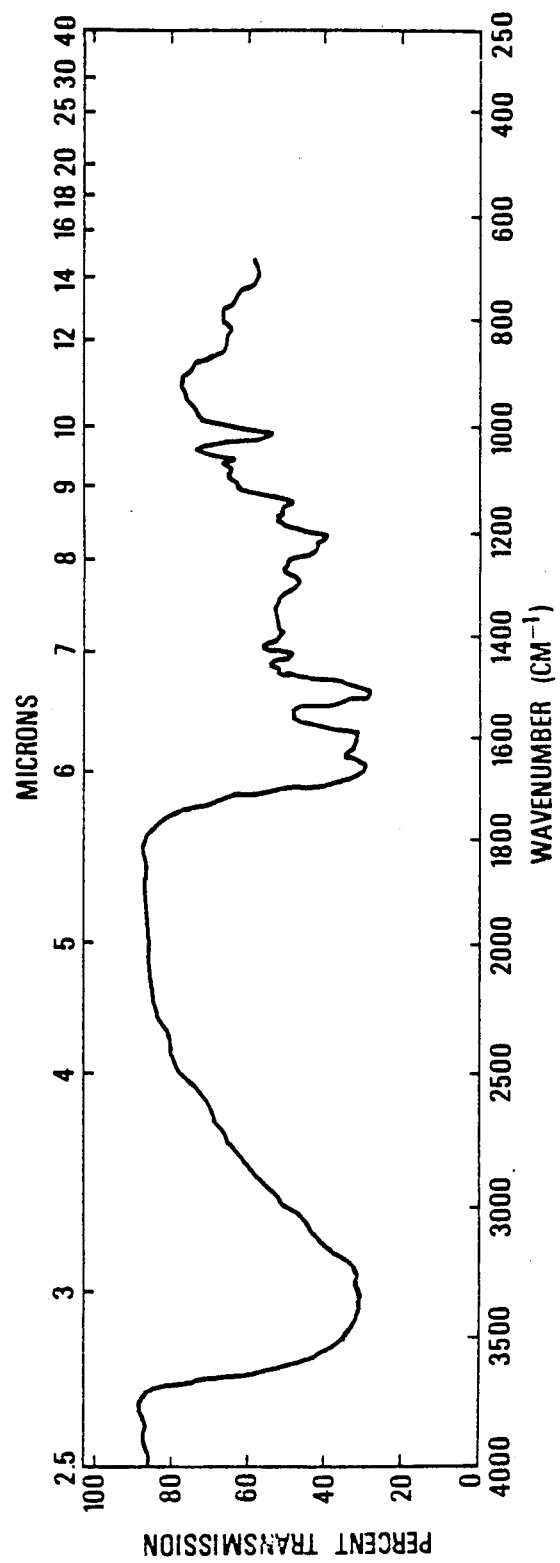

The infrared absorption spectrum of antibiotic A41030 factor E in KBr pellet is shown in the accompanying drawings as FIG. 5. The following distinguishable absorption maxima are observed: 3448-3226 (strong, broad), 1653 (strong), 1600 (medium), 1504 (strong), 1429 (weak), 1198 (medium), 1136 (weak), 1064 (weak), and 1010 (strong) cm$^{-1}$.

The ultraviolet absorption maxima of A41030 factor E in neutral, acidic, and basic methanol:water (1:1) are recorded in Table 5 above.

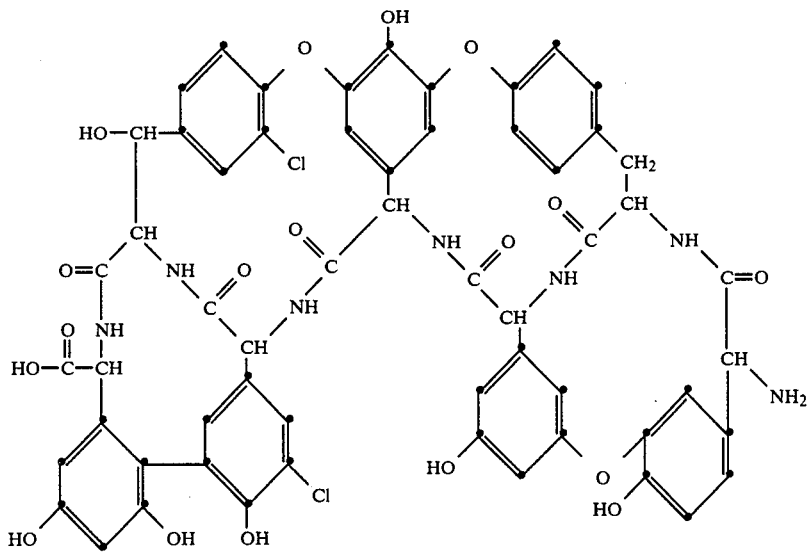

plus one or more n-butyl groups.

A41030 FACTOR E

Antibiotic A41030 factor E is a white solid having an approximate elemental analysis as follows: 56.06% carbon, 4.06% hydrogen, 8.53% nitrogen, 3.50% chlorine, Antibiotic A41030 factor E is soluble in the same solvents as factor A.

On the basis of the observed physical chemical data, the following structure has been assigned to A41030 factor E.

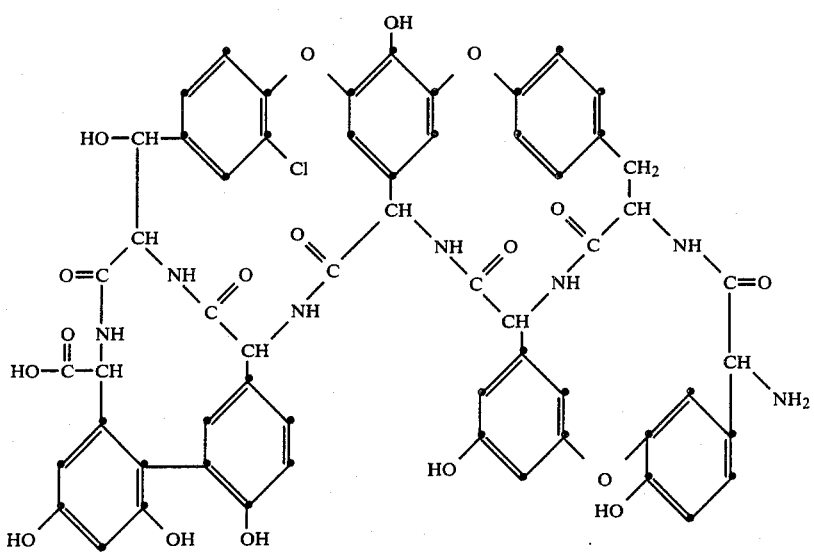

A41030 FACTOR F

Antibiotic A41030 factor F is a white solid having an approximate elemental analysis as follows: 51.39% carbon, 3.96% hydrogen, 6.45% chlorine, 6.45% nitrogen, and 28.65% oxygen. Electrometric titration of factor F in 66% dimethylformamide in water indicated the presence of two titratable groups at $pK_a$ values of about 5.4 and 7.1, respectively, with possibly additional $pK_a$'s>10 (initial pH 5.93). An observed molecular weight of about 1555 was obtained using fast atom bombardment mass spectrometry. A tentative empirical formula of $C_{70}H_{64}Cl_3N_7O_{28}$ is assigned to factor F.

The molecular weight data suggest that factor F differs from factor A by the addition of two sugar moieties, and an uneven molecular weight indicates there is no amino sugar present.

Figure 6:
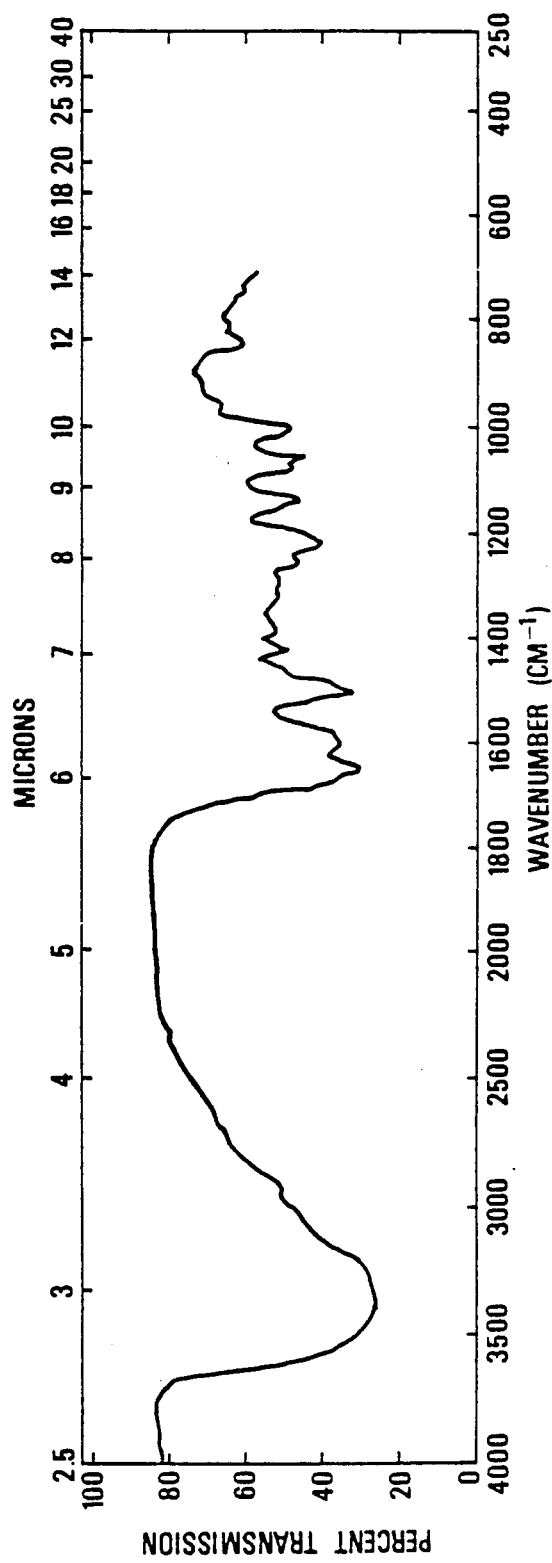

The infrared absorption spectrum of antibiotic A41030 factor F in KBr pellet is shown in the accompanying drawings as FIG. 6. The following distinguishable absorption maxima are observed: 3448–3226 (strong, broad), 1653 (strong), 1600 (medium), 1504 (strong), 1429 (weak), 1258 (weak), 1227 (strong), 1136 (strong), 1075 (strong), 1053 (strong), and 1010 (strong) $cm^{-1}$.

The ultraviolet absorption maxima of A41030 factor F in neutral, acidic, and basic methanol:water (1:1) are recorded in Table 5 above.

Antibiotic A41030 factor F is soluble in the same solvents as factor A.

A41030 FACTOR G

Antibiotic A41030 factor G is a white solid having an approximate elemental analysis as follows; 50.02% carbon, 4.61% hydrogen, 4.74% chlorine, 6.11% nitrogen, and 30.70% oxygen. Electrometric titration of factor G in 66% dimethylformamide in water indicated the presence of titratable groups at $pK_a$ values of about 5.4 and 7.0, respectively, with possibly additional $pK_a$'s>10.5 (initial pH 6.32). An observed molecular weight of about 1688 was obtained using fast atom bombardment mass spectrometry.

Figure 7:
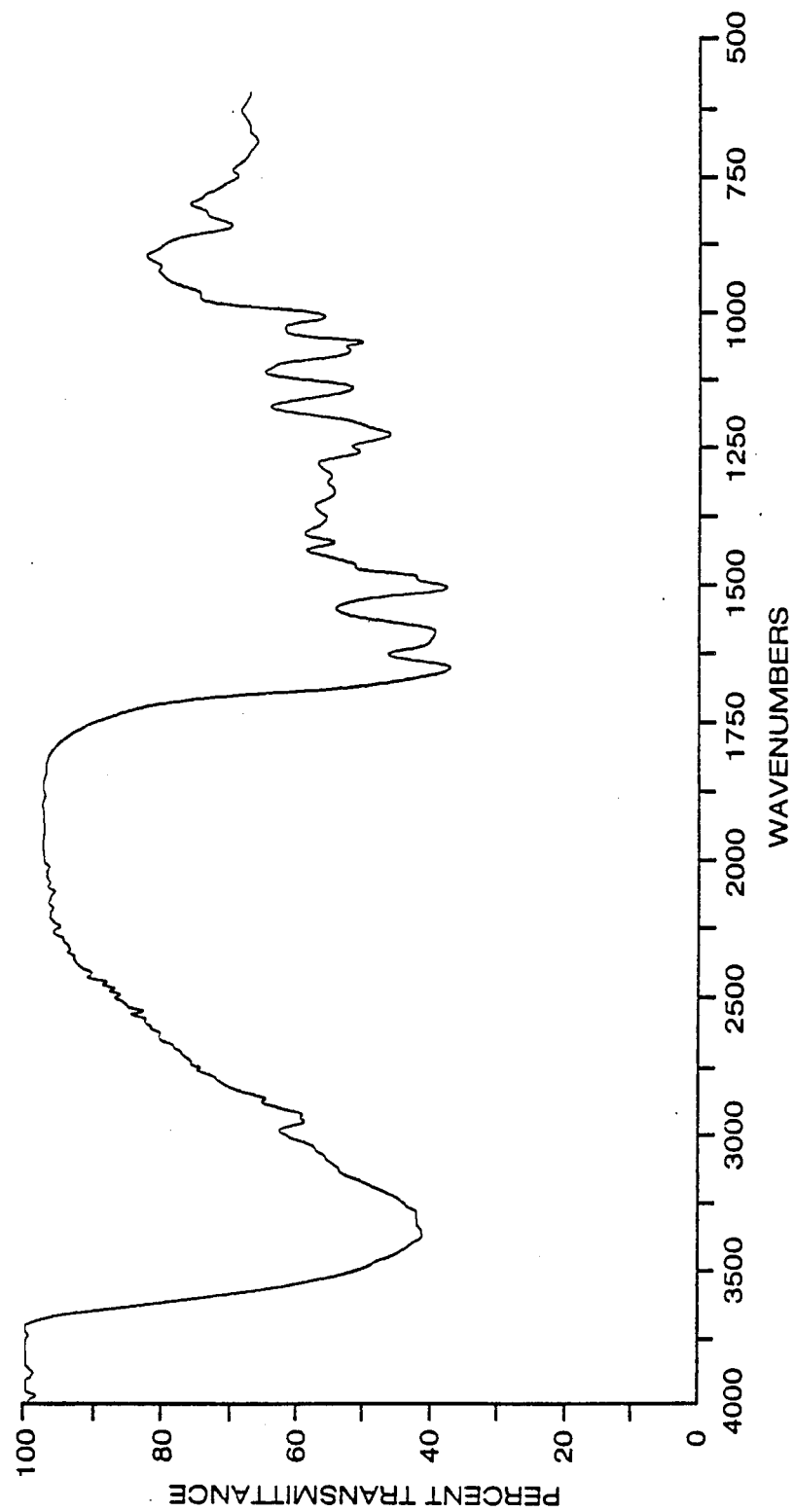

The infrared absorption spectrum of antibiotic A41030 factor G in KBr pellet is shown in the accompanying drawings as FIG. 7. The following distinguishable absorption maxima are observed: 3320 (very broad, strong), 2975 (sharp, weak), 2920 (sharp, weak), 1659 (normal, strong), 1594 (broad, strong), 1512 (sharp, strong), 1492 (shoulder), 1430 (sharp, weak), 1386 (broad, weak), 1337 (broad, weak), 1308 (sharp, weak), 1264 (sharp, weak), 1230 (broad, medium), 1145 (broad, medium), 1077 (sharp, medium), 1062 (sharp, medium), 1014 (sharp, medium), and 846 (broad, medium) $cm^{-1}$.

The ultraviolet absorption maxima of A41030 factor G in neutral, acidic, and basic methanol:water (1:1) are recorded in Table 5 above.

Antibiotic A41030 factor G is soluble in the same solvents as is factor A.

Factors A, B, C, D, E, F, and G of the A41030 complex can be separated and distinguished from one another by employing silica-gel thin-layer chromatography (TLC) and paper chromatography. Bacillus subtilis was the organism used for the bioautography. The ratio of movement (Rx) expressed relative to that of A41030 factor A, which was given a value of 1.00, is set forth in Table 6, which follows.

TABLE 6

| Factor | Rx Solvent System | |
|---|---|---|
| | A | B |
| A | 1.00 | 1.00 |
| B | 0.76 | 0.75 |
| C | 0.68 | 0.44 |
| D | 0.65 | 0.91 |
| E | 0.49 | 0.63 |
| F | 0.21 | 0.25 |
| G | 0.21 | 0.25 |

System A

Paper: Whatman No. 1 (untreated).
Solvent: n-Butanol saturated with water:methanol (1:1).

System B

Sorbent: Merck-Darmstadt-Silica Gel 60.
Solvent: Acetonitrile:ethanol:water (8:1:1.5).

The high performance liquid chromatography (HPLC) retention times of A41030 factors A through G, inclusive, were determined using a stainless steel column having 10 micron LiChrosorb RP-18 as the packing, with a solvent consisting of water:acetonitrile:-dibutylamine (82:18:0.03M) adjusted to pH 2.5 with phosphoric acid. The solvent was applied at a flow rate of 0.75 ml./min. The eluate was monitored by UV absorption at 225 nm. The relative retention values, which are the ratio of the retention time for each factor relative to that of A41030 factor A, are set forth in Table 7, which follows.

TABLE 7

| Factor | Cm. | Min. | Relative Retention |
|---|---|---|---|
| A | 6.4 | 19.2 | 1.00 |
| B | 4.1 | 12.3 | 0.64 |
| C | 5.4 | 16.2 | 0.84 |
| D | 3.8 | 11.4 | 0.59 |
| E | 2.7 | 8.1 | 0.42 |
| F | 4.5 | 13.5 | 0.70 |
| G | 4.5 | 13.5 | 0.70 |

Since the several factors of antibiotic A41030 are amphoteric, containing both an amino group and a carboxylic acid function, they are capable of forming salts with suitable acids and bases. The pharmaceutically acceptable salts so formed are also part of this invention. "Pharmaceutically-acceptable" salts are salts in which the toxicity of the compound as a whole toward warm-blooded animals is not increased relative to the non-salt form. Representative and suitable salts of A41030 factors A, B, C, D, E, F, and G include those acid addition salts formed by standard reaction with both organic and inorganic acids such as, for example, sulfuric, phosphoric, hydrochloric, acetic, succinic, citric, lactic, maleic, fumaric, palmitic, cholic, pamoic, mucic, D-glutamic, d-camphoric, glutaric, glycolic, phthalic, tartaric, lauric, stearic, salicyclic, methanesulfonic, benzenesulfonic, sorbic, picric, benzoic, cinnamic and like acids, as well as salts formed with the carboxylic acid function with such bases as sodium hydroxide, sodium carbonate, potassium carbonate, calcium hydroxide, potassium hydroxide, trimethylamine, ammonium hydroxide, diethanolamine, and like bases.

Antibiotic A41030 complex and factors are active against gram positive microorganisms, including *Staphylococcus* and *Streptococcus* species. These antibiotics also show activity for growth promotion and improving feed efficiency in poultry, swine, and cattle.

The activity of the A41030 complex and the individual factors has been demonstrated by a number of tests which are described hereinafter.

Antibiotic A41030 factors A, B and C have been tested and found to be active against a genus of anaerobic bacteria identified as *Propionibacterium acnes*. The MIC values were determined by the 24-hour agar-dilution method, and are set forth in Table 8, which follows.

TABLE 8

ACTIVITY OF A41030 FACTORS AGAINST *PROPIONIBACTERIUM ACNES*

| Strain of P. acnes | MIC (μg./ml.) | | |
|---|---|---|---|
| | A | B | C |
| 44 | 0.125 | 0.06 | 0.125 |
| 79 | 0.125 | 0.06 | 0.125 |
| 101 | 0.125 | 0.06 | 0.125 |
| 103 | 0.125 | 0.06 | 0.125 |
| 104 | 0.25 | 0.25 | 0.25 |
| 105 | 0.125 | 0.06 | 0.125 |
| 106 | 0.125 | 0.06 | 0.125 |
| 107 | 0.06 | 0.06 | 0.125 |
| 5292 | 0.06 | 0.06 | 0.06 |
| 5170 | ≦0.03 | ≦0.03 | ≦0.03 |
| 5176 | ≦0.03 | 0.06 | ≦0.03 |
| 5187 | ≦0.03 | 0.06 | 0.06 |
| 5191 | 0.125 | 0.06 | 0.125 |
| 5197 | ≦0.03 | 0.06 | ≦0.03 |
| 5226 | 0.5 | 0.5 | 0.125 |
| 5227 | ≦0.03 | 0.06 | 0.06 |
| 5228 | 1.0 | 0.5 | 1.0 |
| 5229 | 0.5 | 0.25 | 0.5 |
| 5246 | 0.06 | 0.125 | 0.06 |

Antibiotic A41030 factors A, B, C, D, E, F, and G have been tested and found to be active against a number of anaerobic bacteria, as recorded in Table 9, which follows, the MIC values having been determined by the agar-dilution method.

TABLE 9

ACTIVITY OF A41030 FACTORS AGAINST ANAEROBIC BACTERIA

| Test Organism | MIC (μg./ml.) | | | | | | |
|---|---|---|---|---|---|---|---|
| | A | B | C | D | E | F | G |
| *Clostridium difficile* 2994 | 32 | 32 | 16 | 0.5 | 0.5 | 1.0 | 2 |
| *Clostridium perfringens* 81 | 0.5 | 0.5 | 1.0 | 0.5 | 1.0 | 1.0 | 2 |
| *Clostridium septicum* 1128 | 2 | 4 | 8 | 0.25 | 0.5 | 1.0 | 2 |
| *Eubacterium aerofaciens* 1235 | >128 | >128 | >128 | 0.5 | 0.5 | 1.0 | 2 |
| *Peptococcus asaccharolyticus* 1302 | ≦0.125 | ≦0.25 | ≦0.25 | ≦0.125 | ≦0.25 | ≦0.25 | 1.0 |
| *Peptococcus prevoti* 1281 | ≦0.25 | ≦0.25 | ≦0.25 | 0.25 | 32 | 32 | 2 |
| *Peptostreptococcus anaerobius* 1428 | ≦0.25 | ≦0.25 | ≦0.25 | 0.5 | 32 | 32 | ≦0.5 |
| *Peptostreptococcus intermedius* 1264 | 1.0 | 0.5 | 0.5 | 1.0 | 32 | 1.0 | 2 |
| *Propionibacterium acnes* 79 | ≦0.25 | 16 | ≦0.25 | 0.25 | 0.5 | 1.0 | 1.0 |
| *Bacteroides fragilis* 111 | 128 | 64 | >128 | 32 | 64 | 32 | 32 |
| *Bacteroides fragilis* 1877 | 32 | 32 | 16 | 32 | 32 | 32 | 32 |
| *Bacteroides fragilis* 1936B | 64 | 32 | 32 | 32 | 64 | 32 | 64 |
| *Bacteroides thetaiotaomicron* 1438 | 64 | 32 | 64 | 32 | 64 | 64 | 64 |
| *Bacteroides melaninogenicus* 1856/28 | >128 | >128 | >128 | >64 | >128 | >128 | >128 |
| *Bacteroides melaninogenicus* 2736 | 4 | 4 | 4 | 0.5 | 32 | 1.0 | 64 |
| *Bacteroides vulgatis* 1211 | 32 | 32 | 32 | 32 | 32 | 32 | 64 |
| *Bacteroides corrodens* 1874 | 64 | 64 | 32 | 32 | 64 | 32 | 32 |
| *Fusobacterium symbiosum* 1470 | 1.0 | 1.0 | 1.0 | 0.5 | 1.0 | 1.0 | 2 |
| *Fusobacterium necrophorum* 6054A | 8 | 8 | 16 | ≦0.125 | 0.5 | 1.0 | 2 |

The A41030 antibiotic factors A, B, C, D, E, F, and G, are also active against a number of strains of *Clostridium difficile*, as determined by the agardilution method. The results of the tests are recorded in Table 10, which follows.

TABLE 10
ACTIVITY OF A41030 FACTORS AGAINST CLOSTRIDIUM DIFFICILE STRAINS

| Clostridium difficile | MIC (μg./ml.) | | | | | | |
|---|---|---|---|---|---|---|---|
| | A | B | C | D | E | F | G |
| 8484 | 1.0 | 1.0 | 1.0 | ≲0.25 | 0.5 | 1.0 | 1.0 |
| 6890 | 1.0 | 1.0 | 2 | 0.5 | 0.5 | 1.0 | 1.0 |
| 2634 | 1.0 | 1.0 | 2 | 0.5 | 1.0 | 2 | 1.0 |
| 78 | 1.0 | 0.5 | 1.0 | ≲0.25 | 0.5 | 1.0 | 1.0 |
| A-194 | 1.0 | 1.0 | 2 | ≲0.25 | 0.5 | 1.0 | 1.0 |
| A-195 | 1.0 | 1.0 | 1.0 | ≲0.25 | 0.5 | 1.0 | 1.0 |
| A-196 | 1.0 | 1.0 | 2 | 0.5 | 1.0 | 2 | 1.0 |
| A-279 | 1.0 | 1.0 | 2 | ≲0.25 | 0.5 | 1.0 | 1.0 |
| A-280 | 1.0 | 0.5 | 1.0 | ≲0.25 | 0.5 | 1.0 | 1.0 |
| A-281 | 1.0 | 1.0 | 2 | 0.5 | 1.0 | 2 | 1.0 |
| WAL-2112 | 1.0 | 1.0 | 2 | ≲0.25 | 0.5 | 1.0 | 1.0 |
| WAL-3657 | 1.0 | 1.0 | 2 | ≲0.25 | 0.5 | 1.0 | 1.0 |
| WAL-4268 | 1.0 | 0.5 | 1.0 | ≲0.25 | 0.5 | 1.0 | 1.0 |
| 107B | 1.0 | 0.5 | 1.0 | ≲0.25 | 0.5 | 1.0 | 1.0 |
| 111F | 1.0 | 1.0 | 2 | ≲0.25 | 0.5 | 2 | 1.0 |
| 1153 | 1.0 | 1.0 | 2 | 1.0 | 1.0 | 2 | 1.0 |
| 3424-5B | 1.0 | 1.0 | 1.0 | 0.5 | 0.5 | 1.0 | 1.0 |
| 3816 | 1.0 | 1.0 | 2 | 0.5 | 0.5 | 1.0 | 1.0 |
| 3950D | 1.0 | 1.0 | 2 | 0.5 | 0.5 | 1.0 | 1.0 |

The in vitro activity of antibiotic A41030 factors A, B, C, D, E, F, and G against a number of aerobic bacteria has been determined using a standard agar-dilution assay. The results after reading the end point after 24 hours are recorded in Table 11, which follows.

TABLE 11
ACTIVITY OF A41030 FACTORS AGAINST AEROBIC BACTERIA

| Test Organism | MIC (μg./ml.) | | | | | | |
|---|---|---|---|---|---|---|---|
| | A | B | C | D | E | F | G |
| Staphylococcus aureus 3055 | 0.125 | 0.125 | 0.5 | 0.25 | 0.125 | 0.5 | 0.5 |
| Staphylococcus aureus V41 | 0.125 | 0.125 | 0.5 | 0.25 | 0.25 | 0.5 | 1 |
| Staphylococcus aureus X400 | 0.5 | 0.25 | 1 | 0.25 | 0.25 | 1 | 2 |
| Staphylococcus aureus S13E | 0.25 | 0.125 | 0.5 | 0.25 | 0.25 | 1 | 1 |
| Staphylococcus epidermidis EPI1 | 0.125 | 0.125 | 0.5 | 0.25 | 0.25 | 0.25 | 0.5 |
| Staphylococcus epidermidis EPI2 | 1 | 0.5 | 2 | 1 | 2 | 2 | 0.5 |
| Streptococcus pyogenes C203 | 0.5 | 0.25 | 1 | 0.5 | 0.25 | 2 | 2 |
| Streptococcus pneumoniae Park I | 0.5 | 0.5 | 1 | 0.5 | 0.25 | 2 | 2 |
| Streptococcus sp. Group D X66 | 1 | 1 | 2 | 1 | 1 | 4 | 4 |
| Streptococcus sp. Group D 9960 | 2 | 1 | 4 | 1 | 1 | 4 | 4 |
| Haemophilus influenzae Brun | 8 | 8 | 16 | — | — | — | — |
| Haemophilus influenzae 251 | 2 | 2 | 4 | — | — | — | — |
| Haemophilus influenzae C.L. | — | — | — | 8 | 8 | 32 | 32 |
| Haemophilus influenzae 76 | — | — | — | 8 | 8 | 32 | 32 |
| Shigella sonnei N9 | >128 | 128 | >128 | >128 | >128 | >128 | >128 |
| Escherichia coli N10 | >128 | 128 | >128 | >128 | >128 | >128 | >128 |
| Escherichia coli EC14 | 128 | 128 | >128 | >128 | >128 | >128 | >128 |
| Escherichia coli TEM | >128 | 128 | >128 | 64 | >128 | >128 | >128 |
| Klebsiella pneumoniae X26 | >128 | >128 | >128 | 128 | >128 | >128 | 64 |
| Klebsiella pneumoniae KAE | >128 | >128 | >128 | >128 | >128 | >128 | >128 |
| Klebsiella pueumoniae X68 | >128 | 128 | >128 | >128 | >128 | >128 | >128 |
| Enterobacter aerogenes C32 | >128 | 64 | >128 | >128 | >128 | >128 | >128 |
| Enterobacter aerogenes EB17 | >128 | >128 | >128 | >128 | >128 | >128 | >128 |
| Enterobacter cloacae EB5 | >128 | 128 | >128 | >128 | >128 | >128 | >128 |
| Enterobacter cloacae 265A | >128 | 128 | >128 | >128 | >128 | >128 | >128 |
| Salmonella typhi X514 | >128 | >128 | >128 | >128 | >128 | >128 | >128 |
| Salmonella typhi 1335 | >128 | >128 | >128 | >128 | >128 | >128. | >128 |
| Pseudomonas aeruginosa X528 | >128 | >128 | >128 | >128 | >128 | >128 | >128 |
| Pseudomonas aeruginosa X239 | >128 | >128 | >128 | >128 | >128 | >128 | >128 |
| Pseudomonas aeruginosa Ps18 | >128 | >128 | >128 | >128 | >128 | >128 | >128 |
| Pseudomonas aeruginosa Ps72 | — | — | — | >128 | >128 | >128 | >128 |
| Serratia marcescens X99 | >128 | 128 | >128 | >128 | >128 | >128 | >128 |
| Serratia marcescens SE3 | >128 | >128 | >128 | >128 | >128 | >128 | >128 |
| Proteus morganii PR15 | >128 | >128 | >128 | >128 | >128 | >128 | >128 |
| Proteus inconstans PR33 | >128 | >128 | >128 | >128 | >128 | >128 | >128 |
| Proteus rettgeri PR7 | >128 | >128 | >128 | — | — | — | — |
| Proteus rettgeri C24 | >128 | >128 | >128 | >128 | >128 | >128 | >128 |
| Citrobacter freundii CF17 | >128 | 128 | >128 | >128 | >128 | >128 | >128 |
| Bordetella bronchiseptica 16 | >128 | >128 | >128 | — | — | — | — |
| Acinetobacter calcoaceticus AC12 | — | — | — | >128 | >128 | >128 | >128 |

— = not tested

The activity of antibiotic A41030 complex against a number of animal pathogens was determined by a standard in vitro antimicrobial broth microtiter test, and the results are set forth in Table 12, which follows.

TABLE 12
ACTIVITY OF A41030 COMPLEX AGAINST SEVERAL ANIMAL PATHOGENS

| Test Organism | MIC (μg./ml.) |
|---|---|
| Staphylococcus sp. 1130 | <0.78 |
| Streptococcus sp. 80 | <0.78 |
| Pasteurella multocida (bovine) | 3.12 |
| Pasteurella hemolytica | 6.25 |
| Bordetella bronchiseptica (Switzer) | 50.00 |
| Escherichia coli | 50.00 |
| Mycoplasma synoviae | 50.00 |
| Mycoplasma hyorhinis | 50.00 |
| Pseudomonas - fish | <0.78 |
| Aeromonas liquefaciens | 50.00 |

All of the A41030 factors tested have shown in vivo antimicrobial activity against experimental bacterial infections. When two doses of test compound were administered subcutaneously to mice in illustrative infections, the activity observed is measured as an $ED_{50}$ value [effective dose in mg./kg. to protect fifty percent of the test animals: See Warren Wick, et al., *J. Bacteriol.* 81, 233-235 (1961)]. The $ED_{50}$ values observed for A41030 factors A, B, C, D, E, and F are given in Table 13, which follows.

TABLE 13

| Antibiotic | Staph. aureus ED$_{50}$ | S. pyogenes ED$_{50}$ | S. pneumoniae ED$_{50}$ |
|---|---|---|---|
| A41030A | 1.4 | 2.8 | 1.68 |
| A41030B | <0.43 | 1.4 | 1.4 |
| A41030C | <0.43 | 10.4 | 6.7 |
| A41030D | 0.339 | 3.24 | 2.21 |
| A41030E | <0.31 | 3.54 | 3.11 |
| A41030F | <0.31 | >5.0 | >5.0 |

The acute toxicity of each of the antibiotic A41030 factors A, B, and C, has been determined in mice and has been found to be >300 mg./kg.

The LD$_{50}$ of each of the antibiotic A41030 factors A, B, and C, has been determined in mice as being >300 mg./kg.

The in vivo oral activity of each of the antibiotic A41030 factors A, B, and C, as determined against *S. pyogenes* in mice, is >300 mg./kg.×2.

In one of its aspects this invention provides a method for treating infections in man or animals which comprises administering to said man or animal a non-toxic antibiotic effective dose of between about 25 mg. and about 2,000 mg. of an A41030 antibiotic factor, or the A-41030 complex, or a pharmaceutically-acceptable, non-toxic salt of said factor or complex.

Factor A, or a pharmaceutically-acceptable non-toxic salt thereof, is preferably used in the treatment of infections in man while in general, the complex of factors or a salt thereof is suitable for use in the treatment of infections in animals.

In the treatment of infections in man the antibiotic factor, preferably factor A, is administered by the parenteral route, e.g., by i.m. injection, or i.v. infusion. For injection, the antibiotic or a pharmaceutically-acceptable salt thereof is dissolved in a physiologically acceptable diluent at the desired concentration and administered. Suitable diluents include for example, Water-for-Injection, 0.9% saline, 5% dextrose, Ringer's solution, or other commonly employed diluent. For administration by i.v. infusion, the antibiotic or salt thereof can be made up in a physiological fluid or dilute nutrient at a suitable concentration; for example, at a concentration between about 5% and about 10%, and slowly infused with the fluid. Alternatively, the antibiotic may be administered by the "piggy-back" method.

The individual factors, combinations of the factors, or the whole complex of factors and the pharmaceutically-acceptable, non-toxic salts thereof can be made up in dosage unit formulations in hermetically sealed vials, sterile, rubber-stoppered vials, or in plastic pouches. Such unit dosage forms can contain excipients such as antioxidants, solubilizing agents, dispersing agents, buffers, and the like. One such dosage unit formulation comprises 100 mg. of factor A, or a pharmaceutically-acceptable salt thereof, in a rubber (butyl rubber) stoppered vial. Another dosage unit formulation comprises 250 mg. of factor A, or a salt thereof, in a sterile, sealed vial. For i.v. infusion a dosage unit formulation of this invention comprises 5 g. of factor A, or a pharmaceutically-acceptable salt thereof, in a plastic pouch.

When A41030 complex or an A41030 factor is used as an antibacterial agent, it may be administered either orally or parenterally. As will be appreciated by those skilled in the art, the A41030 complex or factor is commonly administered together with a pharmaceutically-acceptable carrier or diluent. The dosage of A41030 complex or factor will depend upon a variety of considerations, such as, for example, the nature and severity of the particular infection to be treated. Those skilled in the art will recognize that appropriate dosage ranges and/or dosage units for administration may be determined by considering the MIC and ED$_{50}$ values and toxicity data herein provided, together with factors such as the patient or host and the infecting organism.

The A41030 antibiotics are useful inter alia for suppressing the growth of *Staphylococcus, Streptococcus* and *Propionibacterium acnes* organisms, and the antibiotics could therefore be used, for example, in the treatment of acne. The A41030 individual factors, or mixtures thereof in the purified state, can be formulated in pharmaceutically-acceptable diluents such as isopropyl alcohol for application to the skin. Such solutions can be made up with antibiotic concentrations of from about 1 to about 15 percent weight per volume. Alternatively, the antibiotics can be made up into creams or lotions for application to the skin.

The A41030 antibiotics are also useful for suppressing the growth of *Clostridium difficile* organisms, which cause *Pseudomembranous colitis* in the intestine. The A41030 individual factors or mixtures thereof could be used in the treatment of *Pseudomembranous colitis* by the oral administration of an effective dose of said antibiotics or a pharmaceutically-acceptable, non-toxic salt thereof, prepared in a pharmaceutically-acceptable dosage form. For such use the antibiotic can be administered in gelatin capsules or in liquid suspension.

The antibiotics of this invention also can be used in veterinary medicine in the treatment of infectious diseases in domestic and farm animals. They are useful also in animal husbandry, e.g., in enhancing the growth of beef cattle and other ruminants. An especially valuable use for the antibiotics of this invention resides in their ability to increase the production of milk in dairy cattle. These uses are further aspects of this invention which are described in more detail in the following paragraphs.

The A41030 complex has shown activity against infectious canine hepatitis virus in vitro at 40 mcg./ml. The A41030 complex has also shown activity in vitro against pseudorabies at 20 mcg./ml; and A41030 factor A has shown activity in vitro against pseudorabies at 20 mcg./ml.

The A41030 complex is produced by culturing the previously undescribed microorganism *Streptomyces virginiae* NRRL 12525, or an A41030-producing mutant or variant thereof, in a culture medium containing assimilable sources of carbon, nitrogen, and inorganic salts, under submerged aerobic fermentation conditions until a substantial level of antibiotic activity is produced. Most of the antibiotic activity is generally found in the broth, while minor amounts of antibiotic activity may be associated with the mycelia. The A41030 complex is most readily separated from the fermentation mixture by removal of the mycelia, i.e., the biomass, by filtration. The mycelia are generally discarded. The antibiotic complex is then isolated from the filtered fermentation broth preferably by column chromatography, over a suitable adsorbent using methanol:water (1:1) as the eluting agent.

Suitable adsorbents include carbon, alumina, anion and cation exchange resins, silica gel, polyamide, carboxymethylcelluloses, highly porous copolymers of styrene and divinylbenzene such as Diaion HP-20, the Amberlite XAD resins, and the Duolite resins such as ES-865 and the like, as well as Sephadex resins, the hydrophilic, insoluble, molecular-sieve chromatographic mediums made by cross-linking dextran, and also TSK Gels. The Diaion resins are a product of Mitsubishi Chemical Industries, Limited, Tokyo, Japan. The Amberlite XAD resins are produced by Rohm and Haas, Philadelphia, Pa. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, and from Bio-Rad, 2200 Wright Ave., Richmond, Calif., 94804.

The A41030 antibiotic complex can be further purified and separated into its individual factors by chromatographic techniques.

A number of different media may be used with *Streptomyces virginiae* NRRL 12525, to produce the A41030 complex. For economy in production, optimal yield, and ease of product isolation, however, certain culture media are preferred. These media should contain assimilable sources of carbon, nitrogen, and inorganic salts. Suitable carbon sources include dextrin, starch, mannose, glycerol, and cottonseed oil. Optimum levels of carbon sources are from about 2 to about 3 percent by weight.

Preferred nitrogen sources include soybean grits, soybean flour, peanut meal, fish meal, meat peptone, and pork blood meal.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium., calcium, ammonium, chloride, carbonate, phosphate, sulfate, nitrate and like ions.

Addition to the fermentation medium of Tween 80 (oily liquid polyoxyethylene sorbitan monooleate, a product of ICI Americas, Inc., Wilmington, Del.), at a level of 2–4% serves to increase the yield by about 300%. However, difficulty is experienced in isolating the A41030 antibiotic under these conditions.

Although small quantities of the A41030 antibiotic may be obtained by shake-flask culture, submerged aerobic fermentation in tanks is preferred for producing substantial quantities of the A41030 antibiotic. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a larger tank where, after a suitable incubation time, the A41030 antibiotic is produced in optimal yield.

An alternate method of providing inoculum for the vegetative medium consists of substituting a lyophilized pellet for the aqueous spore suspension. Lyophilized pellets are prepared in a manner known in the art. Preparation of the spore suspension for lyophilization is similar to the preparation of the aqueous spore suspension, except that sterile calf serum is substituted for sterile distilled water.

The A41030-producing organism can be grown over a broad temperature range of from about 10° to about 34° C. Optimum production of A41030 antibiotic complex appears to occur at a temperature of about 30° C.

As is customary in aerobic submerged culture processes, sterile air is dispersed through the culture medium. For efficient growth of the organism, the volume of the air used in tank production is in the range of from about 0.1 to about 0.5 volumes of air per volume of culture medium per minute (v/v/m), with from about 100 to about 300 RPM agitation. An optimum rate in a 165-liter vessel containing 100 liters of fermentation medium is about 0.25 v/v/m, with agitation provided by an impeller rotating at about 200 RPM.

Antibiotic activity is generally present after about 48 hours and remains present for at least 144 hours during the fermentation period. Peak antibiotic production occurs at from about 96 hours to about 120 hours fermentation time.

Production of the A41030 antibiotic can be monitored during the fermentation by either agar diffusion using *B. subtilis,* or a turbidimetric method using *Staphylococcus aureus* ATCC 9144.

In order to illustrate more fully the operation of this invention, the following Examples are provided.

EXAMPLE 1

Preparation of First Stage Inoculum

The following medium was prepared for use in the agar slant culture of *Streptomyces virginiae* NRRL 12525:

| Ingredient | Amount (g./L.) |
| --- | --- |
| Dextrin[1] | 10.0 |
| Yeast extract | 1.0 |
| Enzyme-hydrolyzed casein[2] | 2.0 |
| Beef extract | 1.0 |
| CoCl$_2$.6H$_2$O | 0.01 |
| Agar | 20.0 |
| Deionized water | q.s. to 1 liter |

[1]Matheson Coleman & Bell, Norwood, Ohio 45212
[2]N—Z-Amine A (Humko Sheffield Chemical Co., Memphis, Tenn.).

The pH of the medium as prepared was 6.5, and was adjusted to 7.3 using 5 N aqueous sodium hydroxide before autoclaving. After autoclaving, the pH of the medium was 6.9.

Spores of *Streptomyces virginiae* NRRL 12525 were inoculated on an agar slant made up of the above-identified ingredients, and the thus-inoculated slant was incubated for about six days at a temperature of about 30° C. The mature slant culture was then covered with sterile distilled water and scraped with a sterile tool to loosen the spores and the mycelium. One milliliter of the resulting spore suspension was used to inoculate 50 ml. of vegetative medium. An alternate method of providing inoculum for the vegetative medium consisted of substituting a lyophilized pellet for the aqueous spore suspension. The composition of the vegetative medium was as follows:

| Ingredient | Amount (g./L.) |
| --- | --- |
| Glucose | 20.0 |
| Soybean grits (or soybean flour) | 15.0 |
| Corn steep liquor | 10.0 |
| CaCO$_3$ | 2.0 |
| Tap water | q.s. to 1 liter |

The unadjusted pH of the medium was 5.5, which was adjusted to pH 6.5 with 5 N aqueous sodium hydroxide before autoclaving. The pH of the medium after autoclaving was 7.0.

The vegetative inoculum was incubated in a 250 ml. wide-mouth Erlenmeyer flask containing 50 ml. of medium at about 30° C. for about 48 hours on a shaker rotating through an arc 2 inches in diameter at 250 RPM. This incubated medium is used either to inoculate small fermenters (the inoculum being approximately 1% per volume of fermenter medium) or to inoculate a second stage medium having the same composition as the vegetative medium for the production of a larger volume of culture.

Fermentation of A41030.4

Fifty milliliters of a production medium was inoculated with 1% (0.5 ml.) of the incubated vegetative medium from above. The production medium had the following composition:

| Ingredient | Amount (g./L.) |
| --- | --- |
| Potato dextrin | 30.0 |
| Soybean grits | 6.0 |
| $K_2HPO_4$ | 1.0 |
| $FeSO_4.7H_2O$ | 0.005 |
| $MgSO_4.7H_2O$ | 1.0 |
| $NaNO_3$ | 1.0 |
| $CaCO_3$ | 4.0 |
| Deionized water | q.s. to 1 liter |

The $K_2HPO_4$ was dissolved in water, the solution sterilized separately, and the requisite amount of the solution added to the other ingredients of the medium that had been autoclaved.

The inoculated fermentation medium, 50 ml., was incubated in a 250-ml. Erlenmeyer flask at about 30° C. for about 4–5 days on a shaker rotating through an arc 2 inches in diameter at 250 RPM.

The *Streptomyces virginiae* NRRL 12525 was also incubated in a fermentation carried out on a larger scale in 165-liter and 1600 gallon tanks using the production medium described immediately hereinabove.

The inoculated production medium was allowed to ferment in a 165-liter fermentation tank containing 100 liters of medium for about 210 hours (8.75 days) at a temperature of about 32° C. The fermentation medium was aerated with sterile air at a rate of 0.25 v/v/m and was stirred with conventional agitators at about 200 RPM.

EXAMPLE 2

Separation of A41030 Antibiotics

Whole fermentation broth (4215 liters), obtained as described in Example 1, was filtered using a filter aid (Hyflo Supercel, a diatomaceous earth, Johns-Manville Products Corporation) in a filter press. The filtered broth was applied to a column containing 100 L. of Diaion HP-20 (a highly porous styrene-divinylbenzene copolymer in bead form, Mitsubishi Chemical Industries, Limited, Tokyo, Japan) at a flow rate of 4 L./min. The column was washed successively with 300 L. of water and 1000 L. of methanol:water (1:3) at a rate of 4 L./min. Elution was performed with methanol:water (1:1) at the rate of 6 L./min., collecting 100-L. fractions. Each fraction was analyzed for biological activity. The bioassay was performed by a paper disc assay on agar plates seeded with *Bacillus subtilis*. Fraction 1 was discarded. Fractions 2–15, inclusive, were combined, concentrated under reduced pressure, and the concentrate lyophilized to give 220 g. of crude antibiotic complex.

A portion of this complex, 110 g., was dissolved in 5 L. of methanol:water (1:1), by adjustment to pH 10 with aqueous sodium hydroxide, and the mixture was filtered. The filtrate was applied at 50 ml./min. to a 30-L. column (0.2×1 m.) of coarse Sephadex G-50 (a hydrophilic, insoluble, molecular-sieve chromatographic medium, made by cross linking dextran, and sold by Pharmacia Fine Chemicals, Piscataway, N.J. 08854), previously equilibrated with methanol:water (1:1). The column was eluted with methanol:water (1:1) at 50 ml./min., collecting 3-L. fractions. Fractions 1–12, inclusive, were discarded. Fractions 13–24, inclusive, which contained activity against *B. subtilis*, were combined, concentrated under reduced pressure, and lyophilized to give 35.7 g. of the A41030 antibiotic complex.

EXAMPLE 3

Isolation of A41030 Factor A

An 8 g. portion of the A41030 complex from Example 2 was dissolved in 200 ml. of a solvent consisting of water:acetonitrile:sodium chloride (84:16:2 g./L.) and filtered. The filtrate was applied to a stainless steel column (8×100 cm.) packed with 4 L. of 10–20 micron LP-1/$C_{18}$ reversed-phase silica gel which was prepared in our laboratories by a special procedure described in Examples 6 and 7 of U.S. Pat. No. 4,299,763 (Nov. 10, 1981), which published description is hereby incorporated into and made a part of the instant application. The column was part of a Chromatospac Prep-100 unit (Jobin Yvon, 16–18 Rue du Canal 91160 Longjumeau, France). The column was eluted at 60 ml./min. with water:acetonitrile:sodium chloride (84:16:2 g./L.) collecting 480-ml. fractions. The eluate was monitored at 254 nm using an ISCO Model UA-5 UV monitor with a Type 6 optical unit (Instrumentation Specialties Co., Lincoln, Nebr. 68505). Selected fractions were analyzed for the presence of Factor A by analytical high performance liquid chromatography (HPLC) on a 4.6×250 mm. stainless steel column packed in our laboratories with 10 micron LP-1/$C_{18}$ which was prepared in our laboratories by the special procedure described above. The sample was applied with a Rheodyne Model 7120 injection valve (Rheodyne Inc., Berkeley, Calif. 94710). The solvent, consisting of water:acetonitrile: sodium acetate (81:19:0.03M) adjusted to pH 6 with glacial acetic acid, was supplied at 1 ml./min. (1200 psi) by a Milton Roy Duplex Minipump (Laboratory Data Control, Division of Milton Roy Co., Rivera Beach, Fla. 33404). Factor A was detected at 254 nm using an ISCO Model UA-5 UV detector. Fractions 1–51, inclusive, were discarded. Fractions 52–79, inclusive, rich in factor A were combined and concentrated under reduced pressure to a volume of 500 ml. The concentrate was adjusted to pH 8.2 with aqueous sodium hydroxide and filtered. The filtrate was applied at 15 ml./min. to 100 ml. of Diaion HP-20 resin in a column (2.8×22 cm.) previously equilibrated with water. The column was washed with water (400 ml. adjusted to pH 2.5 with formic acid) until no chloride was detected in the wash by precipitation as silver chloride. Elution was performed with water:acetonitrile (8:2) at 15 ml./min., 1 L. fractions. Fractions were analyzed for activity against *B. subtilis*. Crystalline factor A, which formed in fraction 2 upon refrigeration, was recovered by filtration (389.6 mg.). Fraction 1 and the filtrate from fraction 2 were each concentrated under reduced pressure and lyophilized to give 731.8 mg. and 514 mg. of factor A, respectively.

EXAMPLE 4

Isolation of A41030 Factor B

A 1.0 g. portion of the A41030 complex was dissolved in 35 ml. of a solvent consisting of water:acetonitrile:sodium chloride (85:15:2 g./L.) and the solution was applied to a 4.7×45 cm. Michel-Miller high-performance-low-pressure-liquid-chromatography (HPLPLC) glass column (Ace Glass, Inc., Vineland, N.J. 08360) packed in our laboratories with 25–40 micron LiChroprep RP-18 [hydrocarbon phase ($C_{18}$) chemically bonded to silica gel, from MC/B Manufacturing Chemists, Inc., Cincinnati, Ohio]. An FMI valveless piston pump (Fluid Metering Inc., Oyster Bay, N.Y. 11771) was used to elute the column at 21 ml./min. (100 psi), with the same solvent combination used for sample dissolution, collecting 21-ml. fractions. The eluate was monitored at 280 nm using an ISCO Model UA-5 UV detector. Fractions 1–183, inclusive, were discarded. Fractions 184–245, inclusive, rich in factor B, were combined and concentrated under reduced pressure to 25 ml. Concentrates from seven similar purifications were combined, diluted to 1.4 L. with water, and applied at 8–10 ml./min. to 100 ml. of Diaion HP-20 resin in a column, previously equilibrated with water. The column was washed with water (600 ml.) until no chloride was detected in the wash by precipitation as silver chloride. Elution was performed with water:methanol (1:1) at 8–10 ml./min., collecting 300 ml. fractions. Fractions were analyzed for activity against *B. subtilis*. Fractions 1–5 were combined, concentrated under reduced pressure, and lyophilized to give 523 mg. of crude factor B.

A 550 mg. portion of two combined crude preparations of factor B was dissolved in 10 ml. of a solvent consisting of water:acetonitrile:dibutylamine (75:25:0.03M, which solvent had been adjusted to pH 7.8 with phosphoric acid) by addition of tetrabutylammonium hydroxide until solution had been accomplished. The solution was applied to a 2.8×59 cm. Michel-Miller HPLPLC glass column packed with 25–40 micron LiChroprep RP-8 [hydrocarbon phase ($C_8$) chemically bonded to silica gel, from MC/B Manufacturing Chemists, Inc., Cincinnati, Ohio]. Using an FMI pump, the column was eluted at 5 ml./min. (35 psi) with the same solvent combination used for sample dissolution. The eluate was monitored at 254 nm using an ISCO Model UA-5 UV detector. Selected 27-ml. fractions were analyzed for the presence of factor B by analytical HPLC on a 4.6×250 mm. stainless steel column packed with 10 micron LiChrosorb RP-18 (a commercially available, reversed-phase silica gel, manufactured by E. Merck, Darmstadt, Germany). The sample was applied using a Rheodyne Model 7120 injection valve. The solvent, consisting of water:acetonitrile:dibutylamine (82:18:0.03M) adjusted to pH 2.5 with phosphoric acid, was supplied at 1 ml./min. (750 psi) by a Constametric III pump (LDC-Laboratory Data Control, Division of Milton Roy Co., Riviera Beach, Fla. 33404). Factor B was detected at 225 nm using an LDC Spectro Monitor III variable wavelength UV detector. The portion of the RP-8 column eluate from 999–1296 ml., rich in factor B, was concentrated to a volume of 200 ml. The concentrate was diluted to a volume of 500 ml., adjusted to pH 2.0 with phosphoric acid, and sodium chloride (1 mg./ml.) was added as an ionic marker. This solution was applied at 20 ml./min. to 100 ml. of Diaion HP-20 resin in a column (2.8×22 cm.), previously equilibrated with water. The column was washed with water (500 ml.) adjusted to pH 2.5 with aqueous formic acid, until no chloride was detected in the wash by precipitation as silver chloride. The column was then eluted with 1 L. of water:acetonitrile (6:4) at 30 ml./min. The eluate was concentrated under reduced pressure and lyophilized to give 295.6 mg. of crude factor B.

A 285 mg. portion of this preparation was dissolved in 30 ml. dimethylformamide:water (4:6) by heating, cooled to room temperature, and refrigerated, resulting in precipitation of factor B. The precipitate was recovered by filtration, washed with acetone, and dried under vacuum, to yield 84 mg. of factor B.

EXAMPLE 5

Isolation of A41030 Factor C

A 9.0 g. portion of the A41030 complex was dissolved in 200 ml. of a solvent consisting of water:acetonitrile:sodium chloride (83:17:2 g./L.) and the solution was filtered. The filtrate was applied to an 8×100 cm. stainless steel column packed with 4 L. of 10–20 micron LP-1/$C_{18}$ reversed-phase silica gel which was prepared in our laboratories by the special procedure described in Example 3. The column, part of a Chromatospac Prep-100 unit, was eluted at 60 ml./min. with the same solvent combination used for sample dissolution, and 480-ml. fractions were collected. The eluate was monitored at 254 nm using an ISCO Model UA-5 UV detector. Selected fractions were analyzed for the presence of factor C by analytical HPLPLC on an 0.8×30 cm. Michel-Miller glass column packed in our laboratories with 25–40 micron LiChroprep RP-8. The solvent, water:acetonitrile:sodium chloride (84:16:2 g./L.), was supplied at 4 ml./min. by an FMI pump. Factor C was detected at 254 nm using an ISCO Model UA-5 UV detector. Fractions 1–27, inclusive, were discarded. Fractions 28–52, inclusive, rich in factor C, were combined and concentrated under reduced pressure to a volume of 500 ml.

Concentrates from two similar purifications were combined, filtered, and applied at 10 ml./min. to 100 ml. of Diaion HP-20 resin in a column (2.8×22 cm.), previously equilibrated with water. The column was washed with water (2 L.) until no chloride was detected in the wash by precipitation as silver chloride. Elution was performed with 1 L. of water:acetonitrile (6:4) at 15 ml./min. The eluate was concentrated under reduced pressure and lyophilized to give 2.75 g. of a factor C-enriched mixture of factors. A 1.25 g. portion of this mixture was dissolved in 25 ml. of a solvent consisting of water:acetonitrile:dibutylamine (80:20:0.03M, which solvent had been adjusted to pH 7.8 with phosphoric acid) by addition of tetrabutylammonium hydroxide until solution had been accomplished. The sample was applied to a 2.8×59 cm. Michel-Miller glass column packed with 25–40 micron LiChroprep RP-8 and the column was eluted at 4 ml./min., using an FMI pump, with the same solvent combination used for sample dissolution. The eluate was monitored at 254 nm using an ISCO Model UA-5 UV detector. Selected 28-ml. fractions were analyzed for the presence of factor C by analytical HPLC on a 4.6×150 mm. stainless steel column packed in our laboratories with 10 micron Nucleosil $C_{18}$ (a commercially available, reversed-phase silica gel, manufactured by Rainin Instrument Co., Inc., Woburn, Mass. 01801). The sample was applied using a Rheodyne Model 7120 injection valve. The solvent, consisting of water:acetonitrile:sodium acetate (81:19:2 g./L.) adjusted to pH 6 with glacial acetic acid, was supplied at 1 ml./min. by a Milton Roy Duplex Minipump. Factor C was detected at 225 nm using an ISCO Model 1800 variable wavelength UV detector. The portion of the eluate from 4.2–5.1 L., rich in factor C, was concentrated under reduced pressure to a volume of 500 ml.

Concentrates from three similar purifications were combined and dissolved by addition of phosphoric acid to pH 1.7. Sodium chloride (1 mg./ml.) was added as an ionic marker. The sample was applied at 20 ml./min. to 100 ml. of Diaion HP-20 resin in a column (2.8×22 cm.), previously equilibrated with water. The column was washed with aqueous formic acid of pH 2.5 (300 ml.), until no chloride was detected in the wash by precipitation as silver chloride. The column was eluted with L. of water:acetonitrile (6:4) at 30 ml./min. The eluate was collected, concentrated under reduced pressure, and lyophilized to give 0.87 g. of partially purified factor C. This preparation was dissolved in 20 ml. of a solvent consisting of water:acetonitrile: dibutylamine (80:20:0.03M, which solvent had been adjusted to pH 7.8 with phosphoric acid) by addition of tetrabutylammonium hydroxide until solution had occurred. The sample was chromatographed on 25–40 micron LiChroprep RP-8 in a 2.8×59 cm. Michel-Miller glass column, as previously described. The portion of the eluate from 2.45–3.20 L. was concentrated under reduced pressure to a volume of 500 ml.

Concentrates from two similar purifications were combined and desalted on a column containing Diaion HP-20 resin in the fashion previously described. The eluate was concentrated under reduced pressure and lyophilized to give 688 mg. of factor C. A 678 mg. portion of this preparation was dissolved in 60 ml. water:acetonitrile (6:4) by heating. The solution was cooled and factor C precipitated upon refrigeration. The precipitate was recovered by filtration, washed with acetone, and dried under vacuum to give 428 mg. of factor C.

EXAMPLE 6

Isolation of A41030 Factor D

A 6.0 g. portion of the A41030 complex was dissolved in 200 ml. of a solvent consisting of water: acetonitrile:sodium chloride (83:17:2 g./L.) and the solution filtered. The filtrate was applied to an 8×100 cm. stainless steel column packed with 4 L. of 10–20 micron LP-1/$C_{18}$ reversed-phase silica gel which was prepared in our laboratories by the special procedure described in Example 3. The column, part of a Chromatospac Prep-100 unit, was eluted at 60 ml./min., with the same solvent combination used for sample dissolution, and 480-ml. fractions were collected. The eluate was monitored at 254 nm using an ISCO Model UA-5 UV detector. Selected fractions were analyzed for the presence of Factor D by analytical HPLPLC on an 0.8×30 cm. Michel-Miller glass column packed in our laboratories with 25–40 micron LiChroprep RP-8. The solvent, water:acetonitrile:sodium chloride (84:16:2 g./L.), was supplied at 4 ml./min. using an FMI pump. Factor D was detected at 254 nm using an ISCO Model UA-5 UV detector. Fractions 1–34, inclusive, were discarded. Fractions 35–53, inclusive, rich in factor D, were combined and concentrated under reduced pressure to a volume of about 500 ml.

Concentrates from two similar purifications were combined, diluted to 3 L. with water, and applied at 8–10 ml./min. to 100 ml. of Diaion HP-20 resin in a column (2.8×22 cm.), previously equilibrated with water. The column was washed with water (300 ml.) until no chloride was detected in the wash by precipitation as silver chloride. Elution was performed with L. of a solvent consisting of water:acetonitrile (6:4) at 8–10 ml./min. The eluate was concentrated under reduced pressure and lyophilized to give 2.33 g. of a factor D-enriched mixture of factors.

A 1.15 g. portion of this mixture was dissolved in 25 ml. of a solvent consisting of water: acetonitrile:dibutylamine (80:20:0.03M, which solvent had been adjusted to pH 7.8 with phosphoric acid) by addition of tetrabutylammonium hydroxide until solution occurred. The sample was applied to a 2.8×59 cm. Michel-Miller glass column packed with 25–40 micron LiChroprep RP-8, and the column was eluted at 5 ml./min., using an FMI pump, with the same solvent combination used for sample dissolution. The eluate was monitored at 254 nm using an ISCO Model UA-5 UV detector. Selected 25 ml. fractions were analyzed for the presence of factor D by analytical HPLC on a 4.6×25 mm. stainless steel column packed with 10 micron LiChrosorb RP-18 (a commercially available, reversed-phase silica gel, manufactured by E. Merck, Darmstadt, Germany). The sample was applied using a Rheodyne Model 7120 injection valve. The solvent, consisting of water: acetonitrile:dibutylamine (80:20:0.03M) adjusted to pH 2.5 with phosphoric acid, was supplied at 0.75 ml./min. using a Milton Roy Duplex Minipump. Factor D was detected at 225 nm using an ISCO Model 1800 variable wavelength UV detector. The portion of the eluate from 2.6–3.4 L., rich in factor D, was concentrated under reduced pressure to a volume of 300 ml.

Concentrates from three similar purifications were combined and dissolved by addition of phosphoric acid to pH 7.7. Sodium chloride (1 mg./ml.) was added as an ionic marker. The sample was applied at 20 ml./min. to 100 ml. of Diaion HP-20 resin in a column (2.8×22 cm.), previously equilibrated with water. The column was washed with water (300 ml.) adjusted to pH 2.5 with aqueous formic acid, until no chloride was detected in the wash by precipitation as silver chloride. The column was eluted with 1 L. of water:acetonitrile (6:4) at 30 ml./min. The eluate was concentrated under reduced pressure and lyophilized to give 0.63 g. of partially purified factor D. This preparation was dissolved in 15 ml. of a solvent consisting of water: acetonitrile:dibutylamine (80:20:0.03M, which solvent had been adjusted to pH 7.8 with phosphoric acid) by addition of tetrabutylammonium hydroxide until solution occurred. The solution was chromatographed on 25–40 micron LiChroprep RP-8 in a 2.8×59 cm. Michel-Miller glass column, in the manner previously described. The portion of the eluate from 2.5–3.0 L. was concentrated under reduced pressure to a volume of about 200 ml. This concentrate was desalted on a column containing Diaion HP-20 resin in the fashion previously described. The eluate was concentrated under reduced pressure and lyophilized to give 193 mg. of partially-purified factor D.

A 259 mg. portion of two combined partially purified factor D preparations was dissolved in 6 ml. of a solvent consisting of water:acetonitrile:dibasic sodium phosphate (82:18:0.03M, which solvent had been adjusted to pH 7.8 with phosphoric acid) and adjusted to pH 10 by addition of aqueous 5N NaOH. The solution was applied to a 2.8×59 cm. Michel-Miller glass column packed with 25–40 micron LiChroprep RP-8, and the column was eluted at 4 ml./min., using an FMI pump, with the same solvent combination used for sample dissolution. The eluate was monitored at 254 nm using an ISCO Model UA-5 UV detector. Selected 27-ml. fractions were analyzed for the presence of factor D by analytical HPLC on a 4.6×150 mm. stainless steel column packed in our laboratories with 10 micron Nucleosil $C_{18}$. The sample was applied using a Rheodyne Model 7120 injection valve. The same solvent combination used for the preparative elution was supplied at 0.6 ml./min. by a Milton Roy Duplex Minipump. Factor D was detected at 225 nm using an ISCO Model 1800 variable wavelength UV detector The portion of the eluate from 405–1134 ml. was concentrated under reduced pressure to a volume of 500 ml., and desalted on a column containing Diaion HP-20 resin in the fashion previously described. The eluate was concentrated under reduced pressure and lyophilized to give 120 mg. of factor D.

EXAMPLE 7

Isolation of A41030 Factor E

A 0.3 g. portion of the A41030 complex was dissolved in 30 ml. of a solvent consisting of water: acetonitrile:-sodium chloride (85:15:2 g./L.), and applied to a 2.8×59 cm. Michel-Miller glass column packed in our laboratories with 25–40 micron LiChroprep RP-8. An FMI pump was used to elute the column at 12 ml./min. (85 psi), with the same solvent combination used for sample dissolution, collecting 24-ml. fractions. The eluate was monitored at 254 nm using an ISCO Model UA-5 UV detector. Fractions 1–54, inclusive, were discarded. Fractions 55–122, inclusive, rich in factor E, were combined and concentrated under reduced pressure to a volume of 50 ml.

Concentrates from 13 similar purifications were combined, diluted to 1.5 L. with water, and applied at 5 ml./min. to 100-ml. of Diaion HP-20 resin in a column (2.8×22 cm.), previously equilibrated with water. The column was washed with water (900 ml.) until no chloride was detected in the wash by precipitation as silver chloride. Elution was then performed with water:methanol (1:1) at 10 ml./min., collecting 00-ml. fractions. Fractions were analyzed for activity against *B. subtilis*. Fractions 1–8, inclusive, were combined, concentrated under reduced pressure, and lyophilized to give 1.04 g. of a factor E-enriched mixture of factors. A 0.5 g. portion of this mixture was dissolved in 10 ml. of a solvent consisting of water:acetonitrile:sodium chloride (84:14:2 g./L.), and applied to a 2.8×59 cm. Michel-Miller glass column packed with 25–40 micron LiChroprep RP-8. An FMI pump was used to elute the column at 5 ml./min., with the same solvent combination used for sample dissolution, and 25-ml. fractions were collected. The eluate was monitored at 254 nm using an ISCO Model UA-5 UV detector. Selected fractions were analyzed for the presence of factor E by analytical HPLC on a 4.6×150 mm. stainless steel column packed in our laboratories with 5 micron ODS-Hyperspheres (Shandon Southern Products, Ltd., Cheshire, England). The sample was applied using a Rheodyne Model 7120 injection valve. The solvent, consisting of water-:acetonitrile:sodium acetate (81:19:2 g./L.) adjusted to pH 6 with glacial acetic acid, was supplied at 0.65 ml./min. by a Milton Roy Duplex Minipump Factor E was detected at 225 nm using an ISCO Model 1800 variable wavelength UV detector. The portion of the eluate from 1520–1780 ml. was concentrated under reduced pressure to a volume of 50 ml.

Concentrates from three similar purifications were combined, diluted to 1 L. with water, and applied at 10 ml./min. to 100-ml. of Diaion HP-20 resin in a column (2.8×22 cm.), previously equilibrated with water. The column was washed with water (200 ml.) adjusted with aqueous formic acid to pH 2.5, until no chloride was detected in the wash by precipitation as silver chloride. Elution was performed with 0.5 L. of water:acetonitrile (6:4) at 15 ml./min. The eluate was concentrated under reduced pressure and lyophilized to give 202.2 mg. of partially purified factor E. This preparation was dissolved in 4 ml. of a solvent consisting of water:acetonitrile:sodium chloride (86:14:2 g./L.) and chromatographed at 4 ml./min. on a 2.8×59 cm. Michel-Miller glass column, packed with 25–40 micron LiChroprep RP-8, as previously described. The portion of the eluate from 2060–2480 ml., rich in factor E, was concentrated under reduced pressure to a volume of 50 ml. Concentrates from three similar purifications were combined and desalted on 100-ml. of Diaion HP-20 resin in a column, as previously described. The eluate was concentrated under reduced pressure and lyophilized to give 242 mg. of factor E.

Example 8

Isolation of A41030 Factor F

A 9.0 g. portion of the A41030 complex was dissolved in 200 ml. of a solvent consisting of water: acetonitrile:-sodium chloride (83:17:2 g./L.) and the solution was filtered. The filtrate was applied to an 8×100 cm. stainless steel column packed with 4 L. of 10–20 micron LP-1/$C_{18}$ reversed-phase silica gel which was prepared in our laboratories by the special procedure described in Example 3. The column, part of a Chromatospac Prep-100 unit, was eluted at 60 ml./min., with the same solvent combination used for sample dissolution, and 480-ml. fractions were collected. The eluate was monitored at 254 nm using an ISCO Model UA-5 UV detector. Selected fractions were analyzed for the presence of factor F by analytical HPLPLC on an 0.8×30 cm. Michel-Miller glass column packed in our laboratories with 25–40 micron LiChroprep RP-8. The solvent, water:acetonitrile:sodium chloride (84:16:2 g./L.), was supplied at 4 ml./min. by an FMI pump. Factor F was detected at 254 nm using an ISCO Model UA-5 UV detector. Fractions 1–25, inclusive, were discarded. Fractions 26–36, inclusive, rich in factor F, were combined and concentrated under reduced pressure to a volume of about 500 ml.

Concentrates from three similar purifications were combined, filtered, and the filtrate applied at 10 ml./min. to 100-ml. of Diaion HP-20 resin in a column (2.8×22 cm.), previously equilibrated with water. The column was washed with water (900 ml.) until no chloride was detected in the wash by precipitation as silver chloride. Elution was performed with 1 L. of water-:acetonitrile (6:4) at 15 ml./min. The eluate was concentrated under reduced pressure and lyophilized to give 2.6 g. of partially purified factor F. 500 mg. portion of this preparation was dissolved in 10 ml. of a solvent consisting of water:acetonitrile: sodium chloride (84:16:2 g./L.), by adjustment to pH 7.0 with aqueous sodium hydroxide. The solution was applied to a 4.7×45 cm. Michel-Miller glass column packed in our laboratories with 25–40 micron LiChroprep RP-18. An FMI pump was used to elute the column at 6 ml./min., with the same solvent combination used for sample dissolution, and 24-ml. fractions were collected. The eluate was monitored at 254 nm using an ISCO Model UA-5 UV detector. Selected fractions were analyzed for the presence of factor F, using the analytical HPLPLC system previously described. The portion of the eluate from 1940–2520 ml., rich in factor F, was concentrated under reduced pressure to a volume of about 300 ml.

Concentrates from two similar purifications were combined and applied at 10 ml./min. to 100-ml. of Diaion HP-20 resin in a column (2.8×22 cm.), previously equilibrated with water. The column was washed with water (300 ml.) adjusted to pH 2.5 with formic acid, until no chloride was detected in the wash by precipitation as silver chloride. Elution was performed with 0.75 L. of water:acetonitrile (6:4). The eluate was concentrated under reduced pressure and lyophilized to give 299 mg. of factor F.

EXAMPLE 9

Isolation of A41030 Factor G

An 8 g. portion of the A41030 complex from Example 2 was dissolved in 200 ml. of a solvent consisting of water:aceto-nitrile:sodium chloride (84:16:2 g./L.) and filtered. The filtrate was applied to a stainless steel column (8×100 cm.) packed with 4 L. of 10–20 micron LP-1/$C_{18}$ reversed-phase silica gel which was prepared in our laboratories by the special procedure described in Example 3. The column was part of a Chromatospac Prep-100 unit (see Example 3). The column was eluted at 60 ml./min. with water:aceto-nitrile: sodium chloride (84:16:2 g./L.), collecting 80-ml. fractions. The eluate was monitored at 254 nm as described in Example 3. Selected fractions were analyzed for the presence of factor G by an analytical high performance liquid chromatography (HPLC) procedure described in preceding Examples.

Fractions 22-35, inclusive, rich in factor G, were combined and concentrated under reduced pressure to a volume of 500 ml. Concentrates from three similar purifications were combined, adjusted to pH 8.5 with aqueous sodium hydroxide, and filtered. The filtrate was applied at 10 ml./min. to 100 ml. of Diaion HP-20 resin in a column (2.8×22 cm), previously equilibrated with water. The column was washed with water (400 ml. adjusted to pH 2.5 with formic acid) until no chloride was detected in the wash by precipitation as silver chloride. Elution was performed with water:acetonitrile (6:4) at 15 ml./min., collecting 1 L. fractions. Fractions were analyzed for activity against *B. subtilis*. The active fractions were combined, concentrated under reduced pressure, and lyophilized to give 2.85 g. of material.

A 0.5 g. portion of this material was dissolved in 10 ml. of a solvent consisting of water: acetonitrile:-dibutylamine (80:20:0.03M, which solvent had been adjusted to pH 7.8 with phosphoric acid) by addition of dibutylamine until solution had been accomplished (final pH 8.2). The solution was applied to a 2.8×59 cm. Michel-Miller HPLPLC glass column packed with 25–40 micron LiChroprep RP-8 (from MC/B Manufacturing Chemist, Inc., Cincinnati, Ohio).

Using an FMI pump, the column was eluted at 4 ml./min. with the same solvent combination used for sample dissolution. The eluate was monitored at 254 nm using an ISCO Model UA-5 UV detector. Selected 10 ml. fractions were analyzed for the presence of factor G by the analytical HPLC procedure described in preceding Examples.

Fractions 54–74, inclusive, rich in factor G, were combined with fractions from two similar purifications and applied at 10 ml./min. to 100 ml. of Diaion HP-20 resin in a column (2.8×22 cm), previously equilibrated with water. The column was washed with water (300 ml.) adjusted to pH 2.5 with formic acid, until no chloride was detected in the wash by precipitation as silver chloride. Elution was performed with 0.75 L. of water:acetonitrile (6:4). The eluate was concentrated under reduced pressure and lyophilized to give 960 mg. of factor G.

EXAMPLE 10

Sample Preparation for Biological Assay and Quantitative Analysis of A41030 Factor A in Dried Whole Broth One liter of whole broth was concentrated to a volume of 200 ml. and lyophilized to give 31.5 g. of dried whole broth. A 400 mg. sample of the dried whole broth was extracted 3 times with 10 ml. portions of water at pH 8.5. The extracts were combined, concentrated to a volume of 10 ml., and portions of this concentrate used for biological assay. The turbidimetric assay was conducted on a semiautomated system (Autoturb ® microbiological assay system, Elanco) described by N. R. Kuzel and F. W. Kavanaugh in *J Pharmaceut. Sci.* 60(5), 764 and 767 (1971). In testing the A41030 complex, the following test parameters were used: *Staphylococcus aureus* ATCC 9144 in a nutrient broth medium (pH 7), incubated for four hours at 37° C. Test samples and standard were dissolved in methanol:water (1:1). The standard, A41030 factor A, was presented to the Autoturb ® carrousel at concentrations of 0.4, 0.6, 0.9, 1.2, and 1.5 mcg./ml.

One milliliter of the above concentrate was purified by the following procedure to be used for analysis by HPLC.

(a) One C-18 SEP-PACK cartridge was washed with 10 ml. of methanol, using a 10 ml. syringe with a Luer fitting, as known to the art.

(b) Wash the same cartridge with 10 ml. of water.

(c) Apply 1 ml. of the concentrate from above to the cartridge at the rate of approximately 1 ml./min.

(d) Wash the cartridge with 1 ml. of water and blow the cartridge dry.

(e) Elute the cartridge with 1 ml. of a solution of tetrahydrofuran:water (1:1) at about 0.5 ml./min.

(f) Remove the tetrahydrofuran from the eluate in vacuo, or alternatively, under a nitrogen stream, and reconstitute the eluate to a volume of 1 ml. with water.

(g) Analyze the solution by HPLC procedure as described hereinbefore.

The results of the assay for biological activity and the HPLC analysis of the whole broth are recorded in Table 14, which follows.

TABLE 14

Biological Activity and HPLC Analysis of A41030A in Whole Broth

| Sample No. | Wt. | Concentr. of A41030A+ | Total Wt. of Activity* | Total Wt. of A41030A | % of A41030A+ |
|---|---|---|---|---|---|
| 1 | 106.8 kg | 4.42 mg/g | 491 g | 472 g | 96.1 |
| 2 | 146.5 kg | 10.8 mg/g | 1685 g | 1582 g | 93.9 |

*Total biological activity comprised of A41030 factors A, B, C, D, E, F and G.
+As determined by HPLC.

I claim:

1. A method of producing the A41030 antibiotic complex which comprises cultivating *Streptomyces virginiae* NRRL 12525, or an A41030-producing variant or mutant thereof, in a culture medium containing assimilable sources of carbon, nitrogen, and inorganic salts under submerged aerobic fermentation conditions until a substantial amount of antibiotic A41030 activity is produced by said organism in said culture medium and recovering said culture medium having said antibiotic A41030 activity.

2. The method of claim 1 wherein the organism is *Streptomyces virginiae* NRRL 12525.

3. The method of claims 1 or 2 which includes the additional step of separating the A41030 antibiotic from the culture medium.

4. An axenic culture of the microorganism *Streptomyces virginiae* NRRL 12525.

* * * * *